United States Patent
Imai

(10) Patent No.: US 9,189,703 B2
(45) Date of Patent: Nov. 17, 2015

(54) SYSTEMS AND METHODS FOR COLORIMETRIC AND SPECTRAL MATERIAL ESTIMATION

(71) Applicant: CANON KABUSHIKI KAISHA, Tokyo (JP)

(72) Inventor: Francisco Imai, Mountain View, CA (US)

(73) Assignee: Canon Kabushiki Kaisha, Tokyo (JP)

( * ) Notice: Subject to any disclaimer, the term of this patent is extended or adjusted under 35 U.S.C. 154(b) by 155 days.

(21) Appl. No.: 13/887,163

(22) Filed: May 3, 2013

(65) Prior Publication Data
US 2014/0010443 A1   Jan. 9, 2014

Related U.S. Application Data

(60) Provisional application No. 61/669,529, filed on Jul. 9, 2012, provisional application No. 61/736,130, filed on Dec. 12, 2012, provisional application No. 61/793,879, filed on Mar. 15, 2013.

(51) Int. Cl.
| | |
|---|---|
| *G06K 9/00* | (2006.01) |
| *G06K 9/46* | (2006.01) |
| *G01N 21/25* | (2006.01) |
| *G01N 21/31* | (2006.01) |
| *G01J 3/28* | (2006.01) |

(52) U.S. Cl.
CPC ............ *G06K 9/4652* (2013.01); *G01N 21/251* (2013.01); *G01N 21/31* (2013.01); *G01J 3/28* (2013.01)

(58) Field of Classification Search
None
See application file for complete search history.

(56) References Cited

U.S. PATENT DOCUMENTS

| | | | |
|---|---|---|---|
| 5,313,267 A * | 5/1994 | MacFarlane et al. | 356/405 |
| 7,480,083 B2 * | 1/2009 | Takahashi et al. | 358/474 |
| 2003/0072037 A1 * | 4/2003 | Hamilton | 358/3.28 |
| 2007/0064868 A1 | 3/2007 | Kostka | |
| 2010/0202584 A1 | 8/2010 | Wang | |
| 2010/0220835 A1 | 9/2010 | Gibson | |
| 2010/0260416 A1 | 10/2010 | Tsutsumi | |
| 2011/0026021 A1 | 2/2011 | Peterson | |
| 2011/0051206 A1 * | 3/2011 | Sitter et al. | 358/518 |

(Continued)

OTHER PUBLICATIONS

Woo-Yong Jang et al., Data compressive paradigm for multispectral sensing using tunable DWELL mid-infrared detectors, Optical Society of America, vol. 19, No. 20 / Optics Express 19454, Sep. 2011.

(Continued)

*Primary Examiner* — Li Liu
(74) *Attorney, Agent, or Firm* — Canon U.S.A., Inc. IP Division

(57) ABSTRACT

Systems, devices, and methods for generating signatures for an image obtain an image, estimate a spectral image of the obtained image, calculate one or both of a detection component of the image and a residual component of the image, wherein the detection component of the image is based on the spectral image, a spectral-power distribution for a specific illuminant, and spectral sensitivities of a detector, and wherein calculating the residual component of the image is based on the spectral image, the spectral power distribution for the specific illuminant, and the spectral sensitivities of the detector or, alternatively, based on the spectral image and the calculated detection component, and generate an image signature based on one or both of the detection component and the residual component.

20 Claims, 23 Drawing Sheets

(56) References Cited

U.S. PATENT DOCUMENTS

| | | | |
|---|---|---|---|
| 2011/0187095 A1 | 8/2011 | Anouar | |
| 2011/0249788 A1 | 10/2011 | Nuesch | |
| 2012/0148018 A1 | 6/2012 | Sommer, Jr. | |
| 2012/0176507 A1* | 7/2012 | Quan et al. | 348/222.1 |
| 2012/0207404 A1 | 8/2012 | Robles | |
| 2012/0224872 A1 | 9/2012 | Wu | |
| 2012/0248313 A1 | 10/2012 | Karam | |
| 2012/0321180 A1 | 12/2012 | Friedhoff | |

OTHER PUBLICATIONS

T. J. Roper et al., Development of a Hyperspectral Skin Database, WorldComp'12, Jul. 2012.

Gary A. Shaw et al., Spectral Imaging for Remote Sensing, Lincoln Laboratory Journal, vol. 14, No. 1 (2003).

Steven Bergner et al., A tool to create illuminant and reflectance spectra for light-driven graphics and visualization, ACM Transactions on Graphics, vol. V, No. N, May 2008, pp. 1-17.

Mark S. Drew, Sensor Transforms to Improve Metamerism-Based Watermarking, Color Imaging Conference, Nov. 2010.

Jun Jiang et al., Recovering spectral reflectance under commonly available lighting conditions, Computer Vision and Pattern Recognition Workshops (CVPRW), 2012 IEEE Computer Society Conference, Jun. 2012.

Winston H. Hsu et al., Visual Cue Cluster Construction via Information Bottleneck Principle and Kernel Density Estimation, International Conference on Content-Based Image and Video Retrieval (CIVR), Singapore, 2005.

Y. Zhao, R. S. Berns, Image-based spectral reflectance reconstruction using the Matrix R method, Color Research and Application 32, 343-351 (2007).

Y. Zhao et al., Presentation on Image-based spectral reflectance reconstruction using the Matrix R method, Kyungpook National University School of Electrical Engineering and Computer Science (2007).

Roy S. Berns et al., Practical Spectral Imaging Using a Color-Filter Array Digital Camera, Art Spectral Imaging, Jul. 2006.

M. W. Derhak, M. R. Rosen; Spectral colorimetry using LabPQR: An Interim connection space, J. Imaging Sci. Technol. 50, pp. 53-63, 2006.

Qiao Chen, Li Jie Wang, Stephen Westland; A Study of Metameric Blacks for the Representation of Spectral Images, Applied Mechanics and Materials, vol. 55-57, pp. 1116-1121, May 2011.

Shahram Peyvandi, Seyed Hossein Amirshahi; Generalized spectral decomposition: a theory and practice to spectral reconstruction, JOSA A, vol. 28, Issue 8, pp. 1545-1553 (2011).

Francisco Imai, High-Resolution Multi-Spectral Image Archives: A Hybrid Approach, IS&T, 1998.

Thomas Keusen et al., Multispectral Color System with an Encoding Format Compatible to the Conventional Tristimulus Model, Proceedings of the IS&T/SID 1995 Color Imaging Conference: Color Science, Systems and Applications.

* cited by examiner

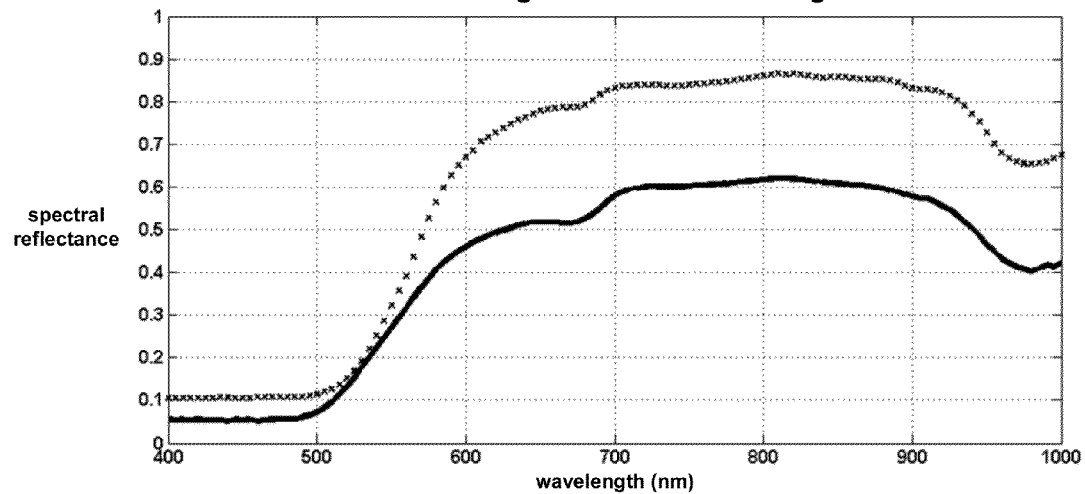
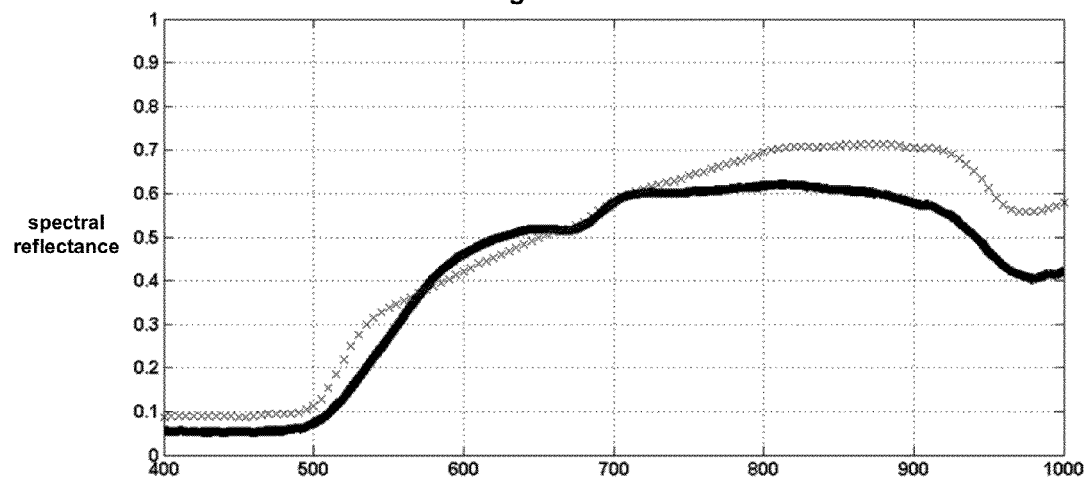
FIG. 6

| Fabric No | Commercial Name | Composition |
|---|---|---|
| 1 | Roc-Lon Budget Blackout Ivory White | 70% polyester 30% cotton |
| 2 | Roc-Lon Renaissance White | 100% cotton |
| 3 | Tablepad White Tablecloth Vinyl | 100% vinyl front side / 100% polyester back side |
| 4 | Home Décor Solid Fabric – Natural Duke | 100% cotton |
| 5 | Signature Series Cable Ivory | 43% polyester 57% cotton |
| 6 | Marine Vinyl PVC Skin Polyester bed | Unknown |
| 7 | Roc-Lon Sonata Sateen White | 50% polyester 50% cotton |
| 8 | Roc-Lon Special Suede Ivory | 70% polyester 30% cotton |
| 9 | Home Décor Solid Fabric – Ivory Pendleton | 42% polyester 57% cotton |
| 10 | Not available | Unknown, possibly cotton |

| Material | 1 | 2 | 3 | 4 | 5 | 6 | 7 | 8 | 9 | 10 |
|---|---|---|---|---|---|---|---|---|---|---|
| 1 | 1 | 0.891<br>0.956<br>0.982 | 0.828<br>0.934<br>0.968 | 0.692<br>0.944<br>0.967 | 0.700<br>0.975<br>0.985 | 0.841<br>0.944<br>0.987 | 0.903<br>0.986<br>0.997 | 0.914<br>0.976<br>0.993 | 0.778<br>0.973<br>0.973 | 0.621<br>0.781<br>0.931 |
| 2 | | 1 | 0.807<br>0.858<br>0.985 | 0.602<br>0.997<br>0.999 | 0.578<br>0.979<br>0.997 | 0.639<br>0.866<br>0.949 | 0.970<br>0.974<br>0.998 | 0.838<br>0.933<br>0.996 | 0.564<br>0.992<br>0.997 | 0.919<br>0.950<br>0.997 |
| 3 | | | 1 | 0.612<br>0.846<br>0.910 | 0.583<br>0.913<br>0.933 | 0.860<br>0.857<br>0.988 | 0.789<br>0.925<br>0.974 | 0.831<br>0.943<br>0.950 | 0.564<br>0.892<br>0.911 | 0.918<br>0.919<br>0.983 |
| 4 | | | | 1 | 0.975<br>0.978<br>0.998 | 0.481<br>0.857<br>0.933 | 0.561<br>0.964<br>0.984 | 0.863<br>0.926<br>0.990 | 0.767<br>0.984<br>0.999 | 0.322<br>0.615<br>0.810 |
| 5 | | | | | 1 | 0.429<br>0.941<br>0.944 | 0.541<br>0.992<br>0.996 | 0.816<br>0.982<br>0.992 | 0.793<br>0.992<br>1.000 | 0.346<br>0.726<br>0.840 |
| 6 | | | | | | 1 | 0.644<br>0.950<br>0.977 | 0.842<br>0.984<br>0.997 | 0.349<br>0.914<br>0.946 | 0.788<br>0.873<br>0.965 |
| 7 | | | | | | | 1 | 0.820<br>0.988<br>0.998 | 0.859<br>0.994<br>0.994 | 0.498<br>0.773<br>0.997 |
| 8 | | | | | | | | 1 | 0.791<br>0.968<br>0.991 | 0.637<br>0.808<br>0.897 |
| 9 | | | | | | | | | 1 | 0.226<br>0.718<br>0.838 |
| 10 | | | | | | | | | | 1 |

FIG. 13

| Material | 1 | 2 | 3 | 4 | 5 | 6 | 7 | 8 | 9 | 10 |
|---|---|---|---|---|---|---|---|---|---|---|
| 1 | 1 | 0.909<br>0.995<br>0.995 | 0.960<br>0.998<br>0.999 | 0.877<br>0.944<br>0.999 | 0.972<br>0.999<br>1.000 | 0.908<br>0.996<br>0.998 | 0.985<br>0.998<br>0.999 | 0.953<br>0.995<br>0.999 | 0.977<br>0.999<br>1.000 | 0.914<br>0.996<br>0.999 |
| 2 | | 1 | 0.784<br>0.999<br>0.999 | 0.968<br>0.978<br>0.999 | 0.911<br>0.989<br>0.999 | 0.767<br>0.983<br>0.999 | 0.966<br>0.999<br>1.000 | 0.899<br>0.980<br>0.986 | 0.9122<br>0.994<br>0.995 | 0.668<br>1.000<br>1.000 |
| 3 | | | 1 | 0.735<br>0.983<br>0.987 | 0.899<br>0.993<br>0.999 | 0.985<br>0.988<br>0.999 | 0.919<br>0.999<br>1.000 | 0.943<br>0.985<br>0.999 | 0.898<br>0.997<br>0.998 | 0.986<br>0.999<br>0.999 |
| 4 | | | | 1 | 0.917<br>0.998<br>0.999 | 0.719<br>0.995<br>0.999 | 0.943<br>0.985<br>0.999 | 0.893<br>0.999<br>1.000 | 0.920<br>0.995<br>0.997 | 0.610<br>0.980<br>0.989 |
| 5 | | | | | 1 | 0.886<br>0.993<br>0.995 | 0.969<br>0.994<br>0.999 | 0.989<br>0.999<br>1.000 | 0.987<br>0.995<br>0.999 | 0.812<br>0.990<br>0.999 |
| 6 | | | | | | 1 | 0.905<br>0.989<br>0.992 | 0.937<br>0.999<br>1.000 | 0.885<br>0.993<br>0.997 | 0.982<br>0.984<br>0.997 |
| 7 | | | | | | | 1 | 0.964<br>0.987<br>0.999 | 0.977<br>0.997<br>0.999 | 0.875<br>0.999<br>1.000 |
| 8 | | | | | | | | 1 | 0.988<br>0.997<br>0.998 | 0.875<br>0.982<br>0.995 |
| 9 | | | | | | | | | 1 | 0.811<br>0.995<br>0.997 |
| 10 | | | | | | | | | | 1 |

FIG. 14

| Material | 1 | 2 | 3 | 4 | 5 | 6 | 7 | 8 | 9 | 10 |
|---|---|---|---|---|---|---|---|---|---|---|
| 1 | 1 | -0.013<br>0.273<br>0.594 | 0.068<br>0.390<br>0.512 | -0.114<br>0.431<br>0.597 | 0.203<br>0.323<br>0.470 | -0.003<br>0.606<br>0.615 | -0.044<br>0.475<br>0.626 | 0.034<br>0.635<br>0.647 | 0.089<br>0.498<br>0.657 | 0.128<br>0.586<br>0.593 |
| 2 | | 1 | 0.045<br>0.054<br>0.720 | -0.023<br>0.375<br>0.691 | 0.110<br>0.468<br>0.665 | -0.019<br>0.380<br>0.502 | -0.039<br>0.414<br>0.799 | 0.079<br>0.590<br>0.678 | -0.001<br>0.589<br>0.754 | 0.047<br>0.410<br>0.699 |
| 3 | | | 1 | 0.170<br>0.230<br>0.391 | 0.112<br>0.346<br>0.426 | 0.145<br>0.393<br>0.605 | 0.170<br>0.199<br>0.596 | 0.265<br>0.336<br>0.646 | -0.008<br>0.197<br>0.668 | 0.117<br>0.249<br>0.764 |
| 4 | | | | 1 | 0.081<br>0.583<br>0.692 | 0.017<br>0.510<br>0.651 | 0.067<br>0.597<br>0.651 | 0.077<br>0.425<br>0.611 | 0.043<br>0.688<br>0.688 | 0.051<br>0.238<br>0.507 |
| 5 | | | | | 1 | 0.091<br>0.556<br>0.643 | -0.074<br>0.580<br>0.619 | -0.061<br>0.362<br>0.476 | 0.237<br>0.514<br>0.625 | 0.229<br>0.236<br>0.604 |
| 6 | | | | | | 1 | -0.036<br>0.515<br>0.578 | 0.068<br>0.436<br>0.621 | 0.177<br>0.664<br>0.669 | 0.111<br>0.324<br>0.581 |
| 7 | | | | | | | 1 | 0.329<br>0.450<br>0.686 | 0.024<br>0.558<br>0.812 | 0.009<br>0.121<br>0.654 |
| 8 | | | | | | | | 1 | -0.045<br>0.652<br>0.665 | 0.304<br>0.462<br>0.689 |
| 9 | | | | | | | | | 1 | 0.066<br>0.194<br>0.622 |
| 10 | | | | | | | | | | 1 |

FIG. 15

| Material | Success rate for overall spectral correlation (%) | Success rate for metameric black correlation (%) |
|---|---|---|
| 1 | 0 | 93.7 |
| 2 | 3.2 | 84.1 |
| 3 | 4.7 | 90.5 |
| 4 | 7.9 | 87.3 |
| 5 | 11.1 | 88.9 |
| 6 | 6.4 | 88.9 |
| 7 | 4.8 | 82.5 |
| 8 | 0 | 85.7 |
| 9 | 9.5 | 82.5 |
| 10 | 15.9 | 85.7 |

FIG. 16

| Category | Human skin | | | Plants: flower | | | |
|---|---|---|---|---|---|---|---|
| Sample | East Asian | South Asian | Caucasian | Yellow rose | Red rose | Pink rose | Violet flower |
| Type | Natural | | | Natural | | | |

| Category | Plants: vegetables | | | | | | | | |
|---|---|---|---|---|---|---|---|---|---|
| Sample | Corn | Carrot | Red tomato | Red onion | Red bell pepper | Orange bell pepper | Green zucchini | Eggplant | Artichoke |
| Type | Natural | | | | | | | | |

| Category | Plants: fruits | | | | | | | | |
|---|---|---|---|---|---|---|---|---|---|
| Sample | Red and Green Apple | Mango | Yellow apple | Banana | Strawberry | Red plum | Orange | Nectarine | Lime and Lemon |
| Type | Natural | | | | | | | | |

| Category | Plants: Leaves | | | | | |
|---|---|---|---|---|---|---|
| Sample | Ivy | Red leaf | Dark green leaf | Grass | Dry grass | Pine leaf |
| Type | Natural | | | | | |

| Category | Wood | | | | Leather | Meat | | Processed food | | |
|---|---|---|---|---|---|---|---|---|---|---|
| Sample | Aspen | Birch | Oak | Pine | 10 samples | Ham | Beef | Cheese | Bread | Cookie |
| Type | Natural | | | | Natural | Natural | | Man-made | | |

| Category | Textile | | | | Paper | | |
|---|---|---|---|---|---|---|---|
| Sample | Red cotton shirt | Green cotton shirt | Blue cotton shirt | White cotton shirt | Blue paper | White paper | Brown office envelope |
| Type | Man-made | | | | Man-made | | |

| Category | Construction | | | | Rocks | | | Others | | | |
|---|---|---|---|---|---|---|---|---|---|---|---|
| Sample | Concrete | Asphalt | Black rubber | White Rubber | Granite | Limestone | White marble | Various soil types (36) | Red aluminum can | Plastic (8) | Paints (81) |
| Type | Man-made | | | | Natural | | | Natural and Man-made | | | |

FIG. 17

| Material | Success rate for overall spectral correlation (%) | Success rate for metameric black correlation (%) |
|---|---|---|
| banana | 63 | 67 |
| carrot | 51 | 64 |
| pink rose | 46 | 63 |
| human skin | 63 | 63 |
| ivy leaf | 53 | 68 |
| pine wood | 62 | 63 |
| ham | 46 | 47 |
| leather | 47 | 65 |
| cookie | 60 | 63 |
| green cotton shirt | 55 | 65 |
| white paper | 58 | 68 |
| asphalt | 53 | 67 |
| white marble | 62 | 65 |
| pink plastic | 47 | 62 |
| wild violet paint | 44 | 67 |

FIG. 22

Graphical representation of a transformation [T]

Graphical representation of the detection components for 192 material samples

Graphical representation of the residual components for 192 material samples

SYSTEMS AND METHODS FOR COLORIMETRIC AND SPECTRAL MATERIAL ESTIMATION

CROSS-REFERENCE TO RELATED APPLICATIONS

This application claims priority to U.S. Provisional Application No. 61/669,529, which was filed on Jul. 9, 2012, to U.S. Provisional Application No. 61/736,130, which was filed on Dec. 12, 2012, and to U.S. Provisional Application No. 61/793,879, which was filed on Mar. 15, 2013.

BACKGROUND

1. Technical Field

The present disclosure generally relates to colorimetric and spectral material estimation.

2. Background

Human beings, as well as digital imaging systems that mimic human vision, capture chromatic signals that can be represented by device-dependent red-green-blue ("RGB") values or device-independent tristimulus values ("XYZ") under specific illumination conditions for a standard observer, resulting in a set of parameters that indicate lightness, hue, and chroma. These illuminant-dependent, observer-dependent color encodings estimate how the human visual system perceives color, as well as how different areas of a scene are encoded as an image by a digital imaging system. Although trichromatic systems give good estimates of the appearances of objects in a scene, they suffer from metamerism, which is a phenomenon in which two different physical stimuli result in identical sets of tristimulus values when integrated with either illuminant spectral-power distribution, detector spectral sensitivities, or both.

SUMMARY

In one embodiment, a method comprises obtaining an image; estimating a spectral image of the obtained image; calculating one or both of a detection component of the image and a residual component of the image, wherein the detection component of the image is based on the spectral image, a spectral-power distribution for a specific illuminant, and spectral sensitivities of a detector, and wherein calculating the residual component of the image is based on the spectral image, the spectral power distribution for the specific illuminant, and the spectral sensitivities of the detector or, alternatively, based on the spectral image and the calculated detection component; and generating an image signature based on one or both of the detection component and the residual component.

In one embodiment, a device for generating a spectral signature comprises one or more computer-readable media and one or more processors configured to cause the device to perform operations including obtaining an image, generating a spectral reflectance estimate of the image, and calculating one or both of a detection component and a residual component, wherein the detection component is based on the spectral reflectance estimate of the image, a spectral-power distribution for a specific illuminant, and detector spectral sensitivities, and wherein the residual component is based on the spectral reflectance estimate of the image and the calculated detection component or, alternatively, based on the spectral reflectance estimate of the image, the spectral power distribution for the specific illuminant, and the detector spectral sensitivities.

In one embodiment, one or more computer-readable media store instructions that, when executed by one or more computing devices, cause the computing device to perform operations comprising obtaining an image; generating a spectral image of the obtained image; and generating one or more of a detection component and a residual component, wherein the detection component is based on the spectral image, a spectral-power distribution for a specific illuminant, and detector spectral sensitivities, and wherein the residual component is based on the spectral image and the calculated detection component or is based on the spectral reflectance image, the spectral power distribution for the specific illuminant, and the detector spectral sensitivities.

BRIEF DESCRIPTION OF THE DRAWINGS

FIG. 6 illustrates the spectral reflectance of certain objects.

FIG. 11 illustrates an example embodiment of a candidate material dataset.

FIG. 13 illustrates examples of spectral reflectance correlations between a material and materials in a candidate material dataset.

FIG. 14 illustrates examples of spectral reflectance correlations between a material and materials in a candidate material dataset.

FIG. 15 illustrates examples of spectral reflectance correlations between a material and materials in a candidate material dataset.

FIG. 16 shows the discrimination success rates for examples of overall spectral correlations and residual component correlations.

FIG. 17 illustrates an example embodiment of a candidate material dataset.

FIG. 22 shows the discrimination success rates for examples of overall spectral correlations and residual component correlations.

DESCRIPTION

The following disclosure describes certain explanatory embodiments. Other embodiments may include alternatives, equivalents, and modifications. Additionally, the explanatory embodiments may include several novel features, and a particular feature may not be essential to some embodiments of the devices, systems, and methods described herein.

Figure 1:
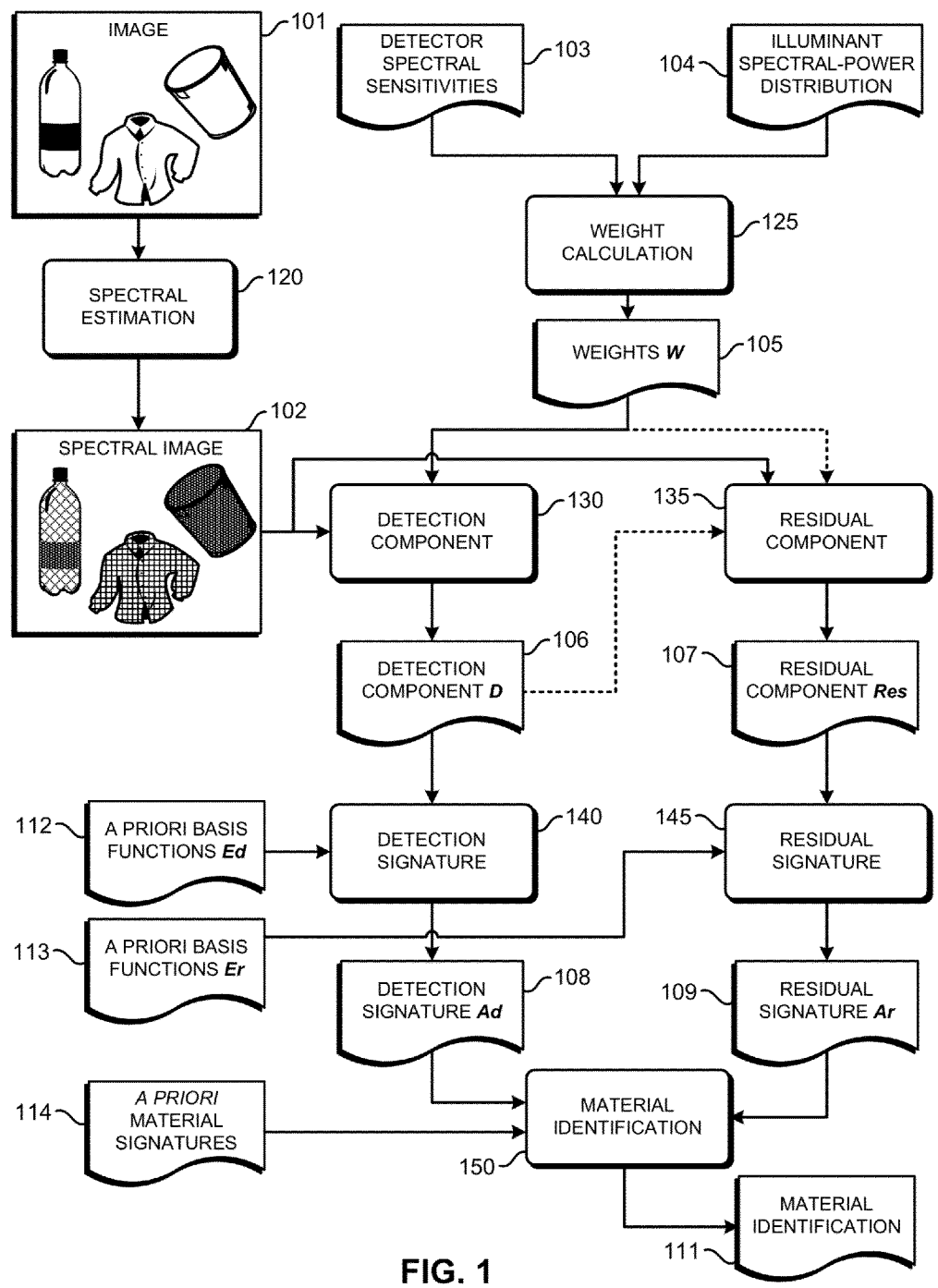
FIG. 1 illustrates an example embodiment of the operations that are performed by a system for material estimation.

FIG. 1 illustrates an example embodiment of the operations that are performed by a system for material estimation. The system includes one or more computing devices (e.g., desktops, laptops, tablets, servers, phones, PDAs), although only certain computing-device components are shown in FIG. 1 in order to emphasize the operations in this illustration.

The system includes a spectral-estimation module 120, which receives one or more images 101 and generates one or more corresponding spectral images 102 from the one or more images 101. An image 101 is an electronic representation of a scene that is captured by converting photons coming from the scene into electrons that produce spatial arrays of a limited number of channels that correspond to captured bands of light wavelengths. Also, although an image is described, the system, as well as the other systems, devices, and methods described herein, can operate on one or more regions of an image. Modules include computer-readable data or computer-executable instructions, and may be implemented in software (e.g., Assembly, C, C++, C#, Java, BASIC, Perl, Visual Basic), hardware (e.g., customized circuitry), or a combination of software and hardware. In some embodiments, the system includes additional or fewer modules, the modules are combined into fewer modules, or the modules are divided into more modules. Though the computing device or computing devices that execute a module actually perform the operations, for purposes of description a module may be described as performing one or more operations.

A spectral image 102 defines values for physical properties that are measured across a range of wavelengths, and thus the values describe a material's physical property that is sampled across a range of wavelengths. Examples of physical properties include spectral reflectance, spectral radiance, spectral scattering, and spectral transmittance. Accordingly, in some embodiments, a spectral image 102 defines spectral reflectance values, which define the ratio of the total amount of light radiation reflected by a surface to the total amount of radiation incident on the surface. Therefore, the spectral image 102 defines the values (e.g., presents a map of the values) of reflectance properties of the material or materials in the image 101. Moreover, some embodiments directly capture the spectral image 102, and thus the obtaining of the image 101 and the spectral estimation module 120 are omitted from these embodiments.

In FIG. 1, a weight-calculation module 125 obtains detector spectral sensitivities information 103, which describes the spectral sensitivities of a detector (e.g., a human observer, an electronic image sensor), obtains illuminant spectral-power distribution information 104, and generates weights W 105 based on the received information. A detection-component module 130 obtains the weights W 105 and the one or more spectral images 102 and generates a detection component D 106 based on them. A residual-component module 135 obtains the one or more spectral images 102, as well as one or more of the detection component D 106 and the weights W 105. Also, the residual-component module 135 generates a residual component Res 107 based on the obtained one or more spectral images 102 and based on the detection component D 106 or the weights W 105.

A detection signature module 140 obtains the detection component D 106 and a priori basis functions Ed 112 and generates a detection signature Ad 108 for the image 101 based on them. A residual signature module 145 obtains the residual component Res 107 and a priori basis functions Er 113 and generates a residual signature Ar 109 for the image 101 based on them. Also, some embodiments use multiple illuminants and detector spectral sensitivities to create several sets of detection component and residual component pairs, which may be used for material identification. Also, one or both of the detection signature Ad 108 and the residual signature Ar 109 may be referred to as an image signature of the image 101.

A material identification module 150 obtains the detection signature Ad 108, the residual signature Ar 109, and a priori material signatures 114 and uses them to generate a material identification 111, for example an estimate of the materials in the one or more images 101.

For example, some embodiments include an a priori table of material signatures created based on representative materials, and the correlation between the joint colorimetric and spectral material signature of a testing material could be used to estimate a probability value for each material in the table. The correlation may be represented as a two-dimensional map in which one axis represents a distance in the detection-signature space between tested samples and candidate materials, and the other axis represents the residual-signature spectral difference between tested samples and candidate materials. The overall metric could be a weighted metric between the distance in detection space and the residual spectral difference.

Thus, the system enables an examination of materials without restricting the examination to parameters calculated based on human visual system properties, but at same time includes an examination that is based on the human visual system.

Figure 2:
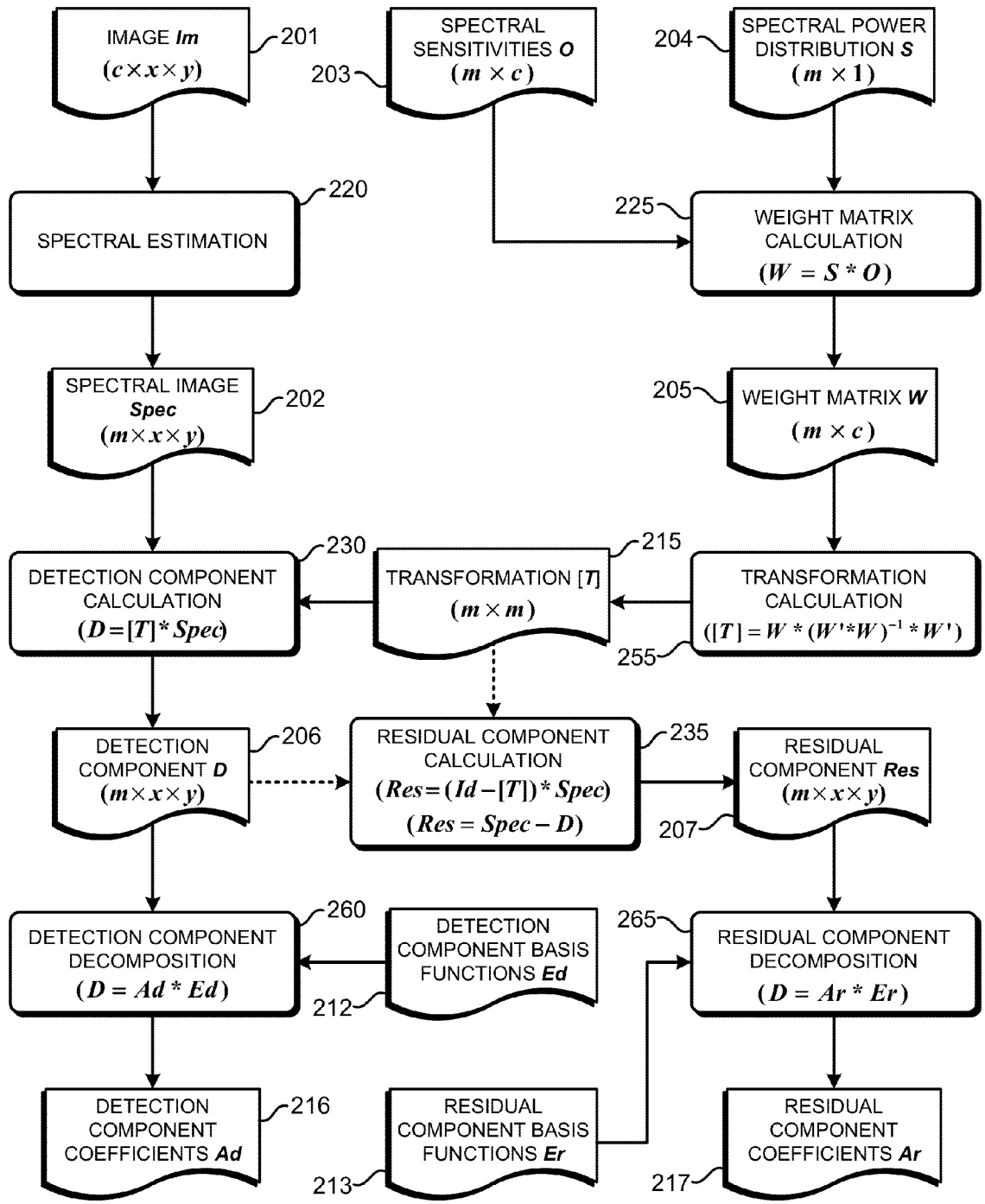
FIG. 2 illustrates an example embodiment a method for generating component coefficients.

FIG. 2 illustrates an example embodiment of the operations that are performed by a system for material estimation. The system receives an image or, alternatively, a region of an image, collectively referred to as "image Im 201," with dimensions c by x by y, where x is the number of rows, y is the number of columns, and c represents the number of channels. The size of the image Im 201 is defined by the dimensions x and y. For example, the image Im 201 could be a 1,000 by 1000 pixel image or a 1 by 1 pixel image. If the image Im 201 is a 1 by 1 pixel image, then the dimensions simplify to c by 1. The image Im 201 is used by the spectral estimation module 220 to generate a spectral image Spec 202 with dimensions m by x by y, where m is the number of reflectance samples for different wavelengths of light. Systems and methods for estimating a spectral image Spec 202 from a multi-channel image Im 201 are described in U.S. Patent Publication No. 20120213407, which is hereby incorporated by reference.

The effect of the combination of illuminant spectral-power distribution and spectral sensitivities of an image acquisition system on the spectral reflectances of the original scene can be mathematically described as a projection of reflectances in the sensing representation space, represented by the channels of the image Im 201 that are captured by a camera. In mathematical terms, the sensing is a transformation [T] 215 (e.g., a projection) that may be calculated as the term-by-term product of the detector spectral sensitivities O 203 (e.g., the spectral sensitivities of the imaging system) and the illuminant spectral-power distribution S 204, for example according to $[T]=W*(W'*W)^{-1}*W'$, where the weight matrix W 205 is an m by c matrix of weights calculated as a term-by-term product between the normalized illuminant spectral-power distribution S 204 (e.g., of a selected illuminant), with dimensions m by 1, and the detector spectral sensitivities O 203, with dimensions m by c; where W' denotes the transposed matrix of the weight matrix W 205; and where the superscript −1 denotes an inverse matrix. The transformation [T] may be defined by a transformation matrix [T].

Thus, in the embodiment illustrated by FIG. 2, a weight matrix calculation module 225 obtains the detector spectral sensitivities O 203 and the illuminant spectral-power distribution S 204 and generates a weight matrix W 205 based on them. To generate the weight matrix W 205, for each channel the term for each of the detector channel sensitivities should be multiplied by the corresponding term in the spectral-power distribution for the same wavelength. For example, the weight matrix W 205 may be calculated according to $$W(i,j)=S(j)*O(j,i),$$

for i=1:c and j=1:m.

A transformation calculation module 255 then generates a transformation [T] 215 based on the weight matrix W 205, where [T] is an m by m matrix. When applied to the spectral image Spec 202, the transformation [T] 215 projects reflectance space into image acquisition space (e.g., the m by x by y space), producing the detection component D 206. The detection component calculation module 230 calculates the detection component D 206 of the captured channels of the image Im 201 according to D=[T]*Spec. The detection component D 206, with dimensions m by x by y, carries the information captured by an image acquisition system under a specific illumination. Therefore, the detection component D 206 is the spectral component of the spectral image that is related to the combination of detector spectral sensitivities and the spectral power distribution of a specified illuminant. Note that the detector spectral sensitivities O 203 of the detector used in the calculation do not have to correspond to the detector that actually captured the image Im 201, but may correspond to a detector (e.g., an imaging sensor) that is determined a priori and is used to build a database of material signatures.

The rejected or ignored residual component Res 207, with dimensions m by x by y, carries no information for the imaging sensor, and the null sensor capture termed is called residual. Therefore, the residual component Res 207 is the spectral component of the spectral image that does not contribute to the detection component. The residual component calculation module 235 can calculate the residual component Res 107 based on the detection component D 206 and the spectral image Spec 202 or based on the transformation [T] 215 (or the weight matrix W 205) and the spectral image Spec 202. For example, the residual component calculation module 235 can calculate the residual component Res 207 according to Res=(Id−[T])*Spec, where Id is an m by m identity matrix. Also, the residual component calculation module 235 can calculate the residual component Res 207 according to Res=Spec−D. Thus, the calculation of the residual component Res 207 does not require the calculation of the detection component D 206, although the calculation of the residual component Res 207 can use the detection component D 206. The residual component Res 207 can be correlated to the spectral curve shapes of respective materials that are not captured by the sensor. In some embodiments, the residual component Res 207 is a metameric black, for example when human-visual-system color-matching functions are considered as detector spectral sensitivities.

Also, the detection component decomposition module 260 decomposes the detection component D 206 based on the detection component D 206 and detection component basis functions Ed 212 to generate the detection component coefficients Ad 216, for example according to D=Ad*Ed. The residual component decomposition module 265 decomposes the residual component Res 207 based on the residual component Res 207 and residual component basis functions Er 213 to generate the residual component coefficients Ar 217, for example according to Res=Ar*Er. Additionally, the basis functions could be calculated, for example, by eigenvector analysis, independent component analysis, etc. Furthermore, one or more of the coefficients Ad 216 and Ar 217 may give a material signature, or the material signature may be otherwise based on Ad 216 and Ar 217. Moreover, considering that surface reflectances may fall within a linear model composed of band-limited functions with a small number of parameters, the spectral component(s) may be decomposed into a small number of components without losing the capability to reconstruct the original spectra.

Additionally, in some embodiments, the operations do not include calculating the residual component Res 207 and the residual component coefficients Ar 217. Furthermore, in some embodiments the operations do not include calculating the detection component D 206 and the detection component coefficients Ad 216.

As a further illustration of the operation of FIG. 2, in an example embodiment the spectral image Spec 202 is a reflectance image Ref 202, which defines spectral reflectance values. Thus, Spec=Ref in this example. Accordingly, the detection component D 206 may be calculated according to D=[T]*Spec, and the residual component Res 207 may be calculated according to Res=(Id−[T])*Spec or Res=Spec−D.

Also, as noted previously, the operations described above could be performed on a pixel basis, for example pixel-by-pixel, in which the variable x corresponding to the row number ranges from x1 to xi, where x1 is the first row and xi is the last row of the image Im 201; and for each row x, the variable y corresponding to the number of the column ranges from y1 to yj, where y1 is the first column and yj is the last column of the image Im 201. The image Im 201 (c,x,y), the spectral image Spec 202 (m,x,y,), the detection component D 206 (m,x,y), and the residual component Res 207 (m,x,y) are general representations of, respectively, a captured image (or region of an image), a spectral image, a detection component, and a residual component. In a case in which x=1 and y=1, then there is only one pixel or is only one pixel sample of an image or of a measurement. A sample taken from a set of samples, represented by dimensions x and y, could be obtained by cropping regions-of-interest in the image, by creating an array of non-contiguous samples in an image, or by performing a calculation on a certain number of images (e.g., a statistical measure, such as mean or median over a sampled number of pixels).

Figure 3:
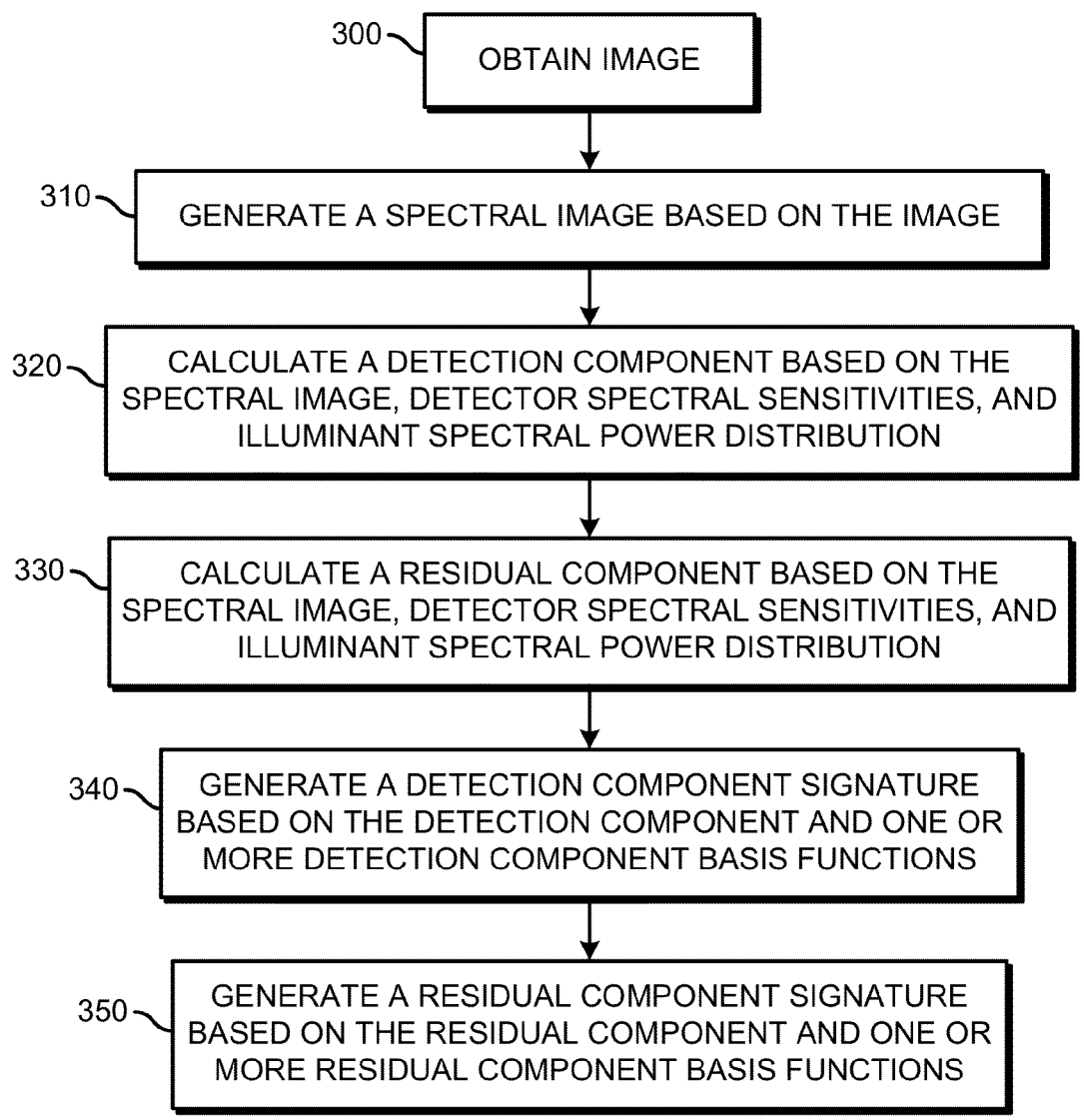
FIG. 3 illustrates an example embodiment of a method for generating component signatures.

FIG. 3 illustrates an example embodiment of a method for generating component signatures. The blocks of this method and the other methods described herein may be performed by one or more computing devices, for example the systems and devices described herein. Also, other embodiments of this method and the other methods described herein may omit blocks, add blocks, change the order of the blocks, combine blocks, or divide blocks into more blocks.

First, in block 300, an image (or a region of an image) is obtained. For example, an image may be received by a computing device. Also, the image may be a multi-spectral image. By capturing several channels with optical filters that have different spectral transmittances, some image-capturing devices sample the spectra in a manner that allows the estimation of the spectral reflectance of objects (e.g., Lambertian objects) in a scene with a relatively high accuracy (e.g., by using the smooth nature of spectral reflectances of objects for data interpolation) based on the captured image.

Next, in block 310, a spectral image is generated based on the image. The flow then moves to block 320, where a detection component is calculated based on the spectral image, one or more detector spectral sensitivities, and illuminant spectral-power distribution. Calculating the detection component may include generating a weight matrix and a transformation. The flow then proceeds to block 330, where a residual component is calculated based on the spectral image, one or more detector spectral sensitivities, and illuminant spectral-power distribution. Calculating the residual component may include generating a weight matrix and a transformation, for example in embodiments that omit block 320. Also, in some embodiments the residual component is calculated based on the spectral image and the detection component. Next, in block 340, a detection-component signature is generated based on the detection component and one or more detection-component basis functions. Finally, in block 350, a residual-component signature is generated based on the residual component and one or more residual component basis functions. Also, some embodiments generate a material signature based on the detection-component signature and the residual-component signature.

Other embodiments of the method may not calculate a detection component, and thus may omit block 340. Some of these other embodiments may include block 320 and calculate the residual component based on the detection component, but some of these other embodiments may also omit block 320. Additionally, other embodiments of the method may not calculate a residual component, and thus may omit blocks 330 and 350.

Figure 4:
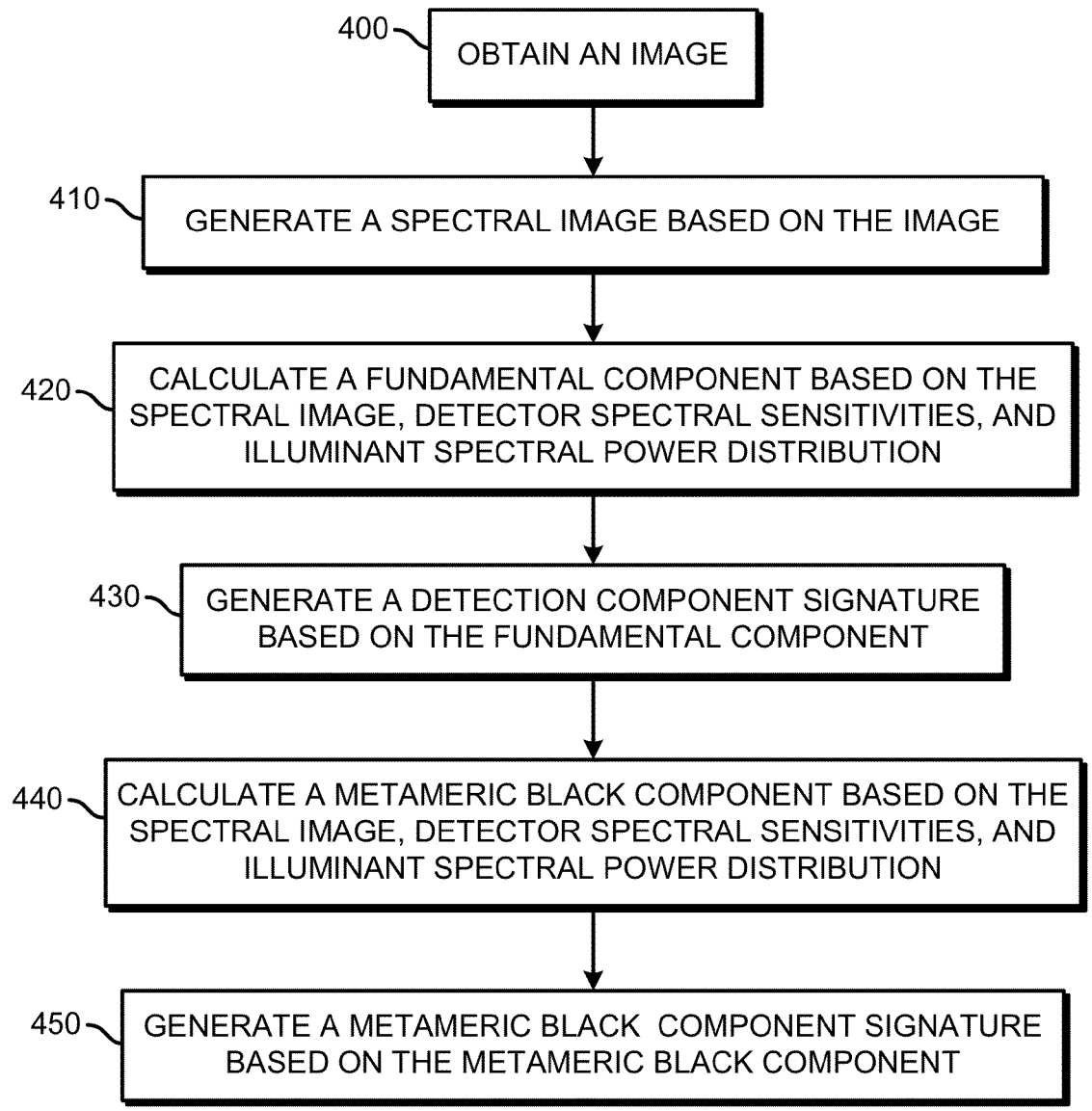
FIG. 4 illustrates an example embodiment of a method for generating component signatures.

FIG. 4 illustrates an example embodiment of a method for generating component signatures. The embodiment illustrated by FIG. 4 calculates a metameric black component for the residual component and calculates a fundamental component for the detection component, although the decomposition into detection and residual components is a more general case than the decomposition into the fundamental component and the metameric black component, and the general case can account for more diverse image acquisition sensitivities.

For example, the Wyszecki fundamental component is a special case of component detection for the human visual system. The Wyszecki fundamental component N is calculated according to N=[R]*Spec, and the metameric black component B is calculated according to B=(I−[R])*Spec or B=Spec−N, where I is an m by m identity matrix. The transformation [R] is calculated according to [R]=A*(A'*A)$^{-1}$*A',
where A is an m by 3 matrix of tristimulus weights that were calculated as a product between the normalized spectral-power distribution S of a selected illuminant and the detector spectral sensitivities O, which are the color matching functions of a human observer (which are an embodiment of detector spectral sensitivities); where A' denotes the transpose matrix of A; and where the superscript$^{-1}$ denotes an inverse matrix. The fundamental component N, with dimensions m by x by y, is the portion that is transmitted by the human visual system and that carries all information necessary for human color sensation. The metameric black component B, with dimensions m by x by y, is portion that is rejected or ignored by the human visual system and that carries no information for human color sensation, but instead evokes the null color "sensation" termed metameric black.

In FIG. 4, the flow starts in block 400, where an image is obtained (e.g., received, captured). Next, in block 410, a spectral image is generated based on the obtained image. The flow then proceeds to block 420, where a fundamental component N is calculated based on the spectral image, detector spectral sensitivities (e.g., the color matching functions of a human observer), and illuminant spectral-power distribution. For example, the fundamental component N may be calculated according to N=[R]*Spec.

The flow then moves to block 430, where a detection component signature is generated based on the fundamental component N. For example, the fundamental component N may be decomposed into its basis function En and their respective coefficients An (e.g., using eigenvector analysis, using independent component analysis), and the detection component coefficients An may be used as the detection component signature.

Next, in block 440, a metameric black component B is calculated based on the spectral image, detector spectral sensitivities (e.g., the color matching functions of a human observer), and illuminant spectral-power distribution. Also, in some embodiments the metameric black component B is calculated based on the spectral image and the fundamental component N.

Finally, in block 450 a residual component signature is generated based on the metameric black component B. For example, the metameric black component B may be decomposed into its basis function Eb and their respective coefficients Ab (e.g., using eigenvector analysis, using independent component analysis), and the metameric black component coefficients Ab may be used as the metameric black component signature.

Figure 5:
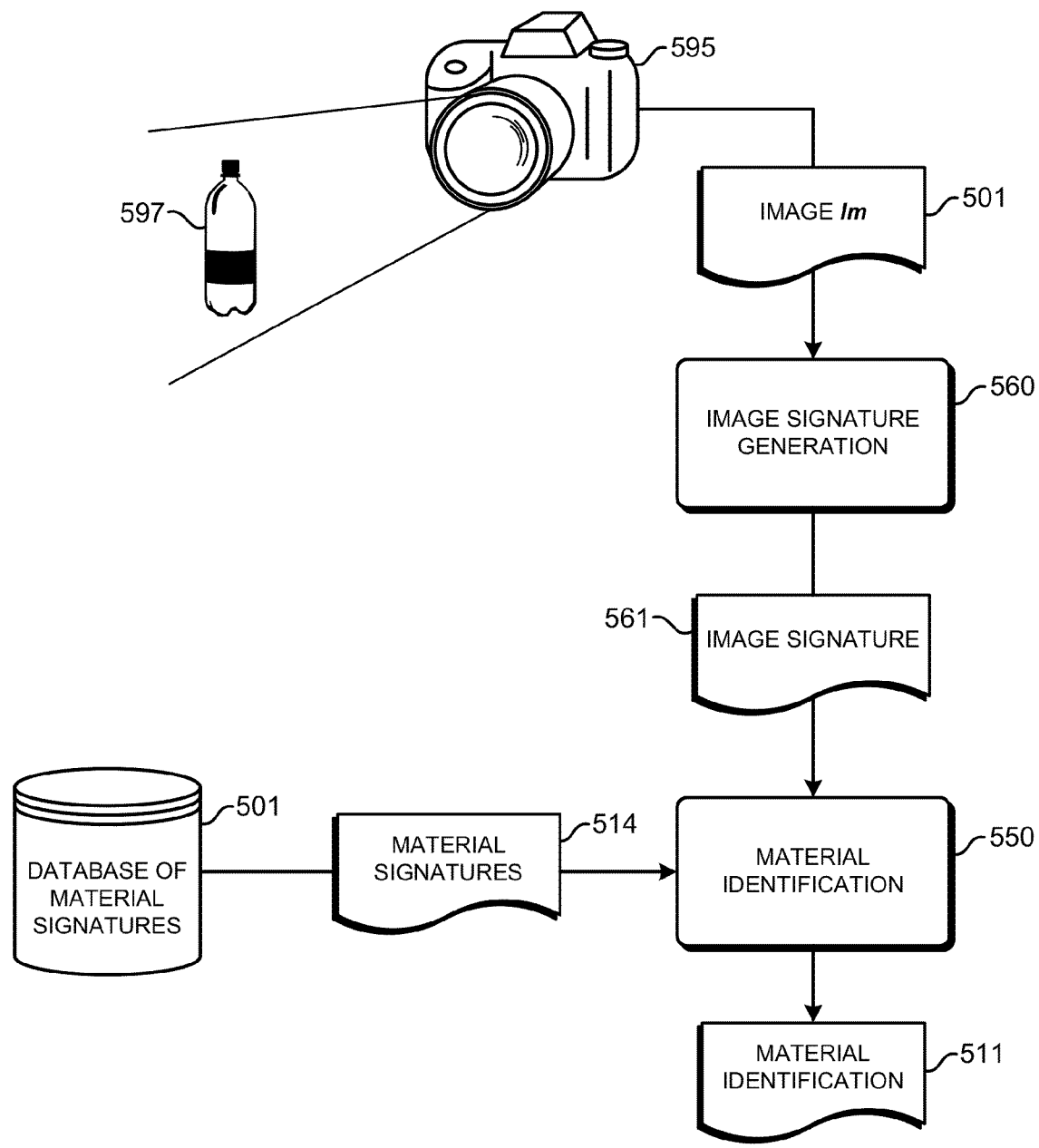
FIG. 5 illustrates an example embodiment of the operations that are performed by a system for material identification.

FIG. 5 illustrates an example embodiment of the operations that are performed by a system for material identification. The system includes one or more cameras (or other image sensors) and one or more computing devices, although only certain components are shown in FIG. 5 in order to emphasize the operations in this illustration. A camera 595 captures an image Im 501 of an object 597. The camera 595 may have tunable sensitivities, may be configured to capture light fields, and may be configured to capture multi-channel images. The image Im 501 is received by an image-signature generation module 560, which may be a component of the camera 595 or a component of a separate device. The image-signature generation module 560 generates an image signature 561 based on the image Im 501. The image signature 561 may include one or more of a detection signature and a residual signature, or may include a combined signature that was generated from the detection signature and the residual signature. The image signature 561 is sent to a material-identification module 550.

The material-identification module 550 also obtains material signature 514 from a database of material signatures 501, which stores previously generated material signatures 514, for example material signatures 514 that were produced by experimental analysis. Based on the image signature 561 and the material signatures 514, the material-identification module 550 generates a material identification 511 that identifies one or more materials in the image, which correspond to the materials of the object 597.

For example, to generate the material identification 511, in some embodiments the material-identification module 550 compares image signatures 561 with pre-determined material signatures 514. An image signature 561 and a pre-determined material signature 514 may each include a respective multi-dimensional representation of their respective materials, and the material-identification module 550 may calculate correlations between the image signature 561 and the pre-determined material signatures 514. The material-identification module 550 may separately evaluate detection component signatures and residual component signatures, or may combine them into a single signature. For example, the material-identification module 550 may compare the detection component signature of a test object with the detection component signature of a reference object (e.g., a candidate object whose information is stored in the database of material signatures 501) and separately compare the residual component signature of the test object with the residual signature of the reference object. Or the material-identification module 550 may use a detection component signature and a residual component signature that are combined into a single material signature and compare the single signature of a test object with the single signature of a reference object.

To calculate correlations, some embodiments calculate a probability function using a very simple equation: $P=(C+1)/2$, where C is the Pearson correlation (i.e., a covariance of the samples divided by the product of the standard deviations for each sample). The probability function may be used for both colorimetric components and spectral components, which may give more flexibility to consider both color visual perception and material spectral ground-truth matching by decoupling colorimetric and spectral components. Separating the color component from the object spectral component may improve discrimination capabilities through use of the residual spectral component because the separation may eliminate color aspects in man-made objects that have a large weight in spectral color signatures when only the overall spectra is used. Also, systems and methods may benefit from using the color component. Therefore, some embodiments use a detection probability function $Pn=(Cn+1)/2$ that is defined based on the detection component Cn correlation, use a residual probability function $Pr=(Cr+1)/2$ is defined based on the residual component Cr correlation, or use both.

For material property discrimination, correlation compares the overall similarity in shapes between two spectral reflectances. Thus, a metric derived based on correlation may be more effective than the root-mean-square ("rms") (also referred to as the "quadratic-means error") technique that is sometimes used in spectral curve comparisons between reference spectra and estimated spectra.

For example, FIG. 6 illustrates the spectral reflectance of certain objects. Graph 1 illustrates the spectral reflectance of a test orange (continuous line) and the spectral reflectance of a reference orange (dotted line). The spectral reflectance of the test orange has a very similar shape to the spectral reflectance of the reference orange. A probability metric generated using correlation gives a match of 91% between these two spectral curves. However, the rms spectral error between these curves is 21%, due to the magnitude shift. Graph 2 illustrates the spectral reflectance of the test orange (continuous line) and the spectral reflectance of a reference banana (dotted line). If the rms spectral error is used as the criterion for matching materials, then the smaller rms spectral error (8%) relative to the test orange reflectance indicates that the material is a "banana". But, although the spectral curves of the test orange and the reference banana are very close to each other (which results in a low spectral rms error), the overall shapes of the spectral curves are very different from each other.

Additionally, when performing the comparison, the detection signature Ad and the residual signature Ar may be weighted. If the visual appearance is more important in the implementation application, the detection signature Ad can be given a larger weight than the residual signature Ar. If the ground-truth information is more important, the residual signature Ar can be assigned a larger weight than the detection signature Ad. In certain applications, both the spectral curve shape and the visual appearance of the object are important (e.g., melanoma detection) and the detection signature Ad and the residual signature Ar are considered as a whole (e.g., equally weighted).

Figure 7:
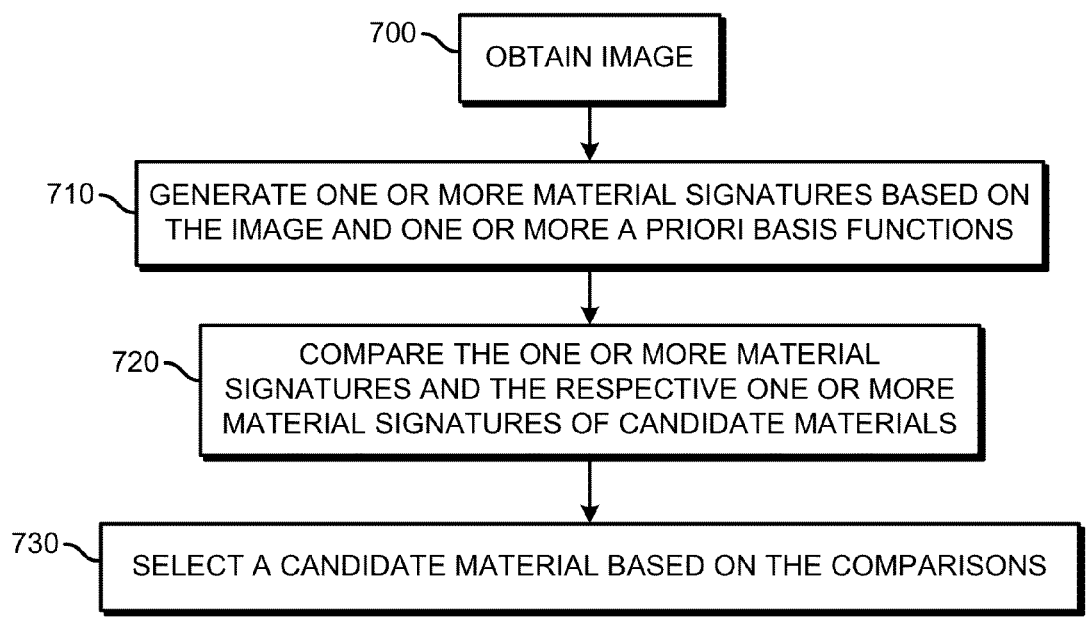
FIG. 7 illustrates an example embodiment of a method for identifying a material.

FIG. 7 illustrates an example embodiment of a method for identifying a material. The flow starts in block 700, where an image (or a region of an image) is obtained. Next, in block 710, one or more material signatures, which may each include one or both of a detection component signature and a residual component signature, are generated based on the image and one or more a priori basis functions.

The flow then moves to block 720, where the one or more material signatures are compared to the respective one or more material signatures of candidate materials, for example by calculating correlations between the one or more material signatures and the respective one or more material signatures of the candidate materials. Finally, in block 730, a candidate material is selected based on the comparisons.

Figure 8:
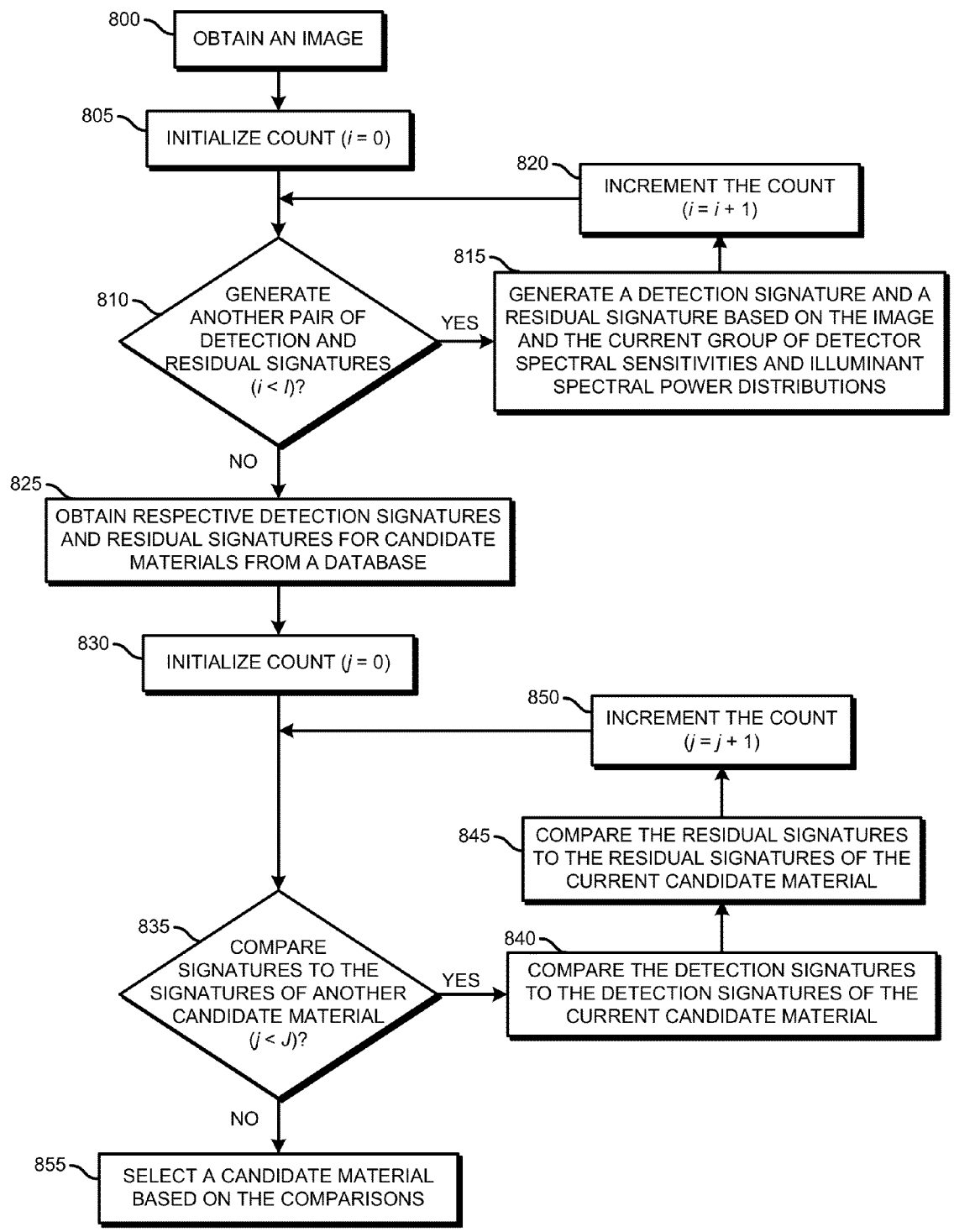
FIG. 8 illustrates an example embodiment of a method for identifying a material.

FIG. 8 illustrates an example embodiment of a method for identifying a material. The flow starts in block 800, where an image is obtained. Next, in block 805, the count i is initialized to 0. The flow then moves to block 810, where it is determined if another pair of a detection signature and a residual signature is to be generated. If there are I groups of spectral sensitivities and illuminant spectral-power distributions for which signatures are to be calculated, then, if i<I (block 810=yes) the flow proceeds to block 815. In block 815, a detection signature and a residual signature are generated based on the image and the current group of detector spectral sensitivities and illuminant spectral-power distributions. The flow then moves to block 820, where the count i is incremented, and then the flow returns to block 810.

If in block 810 it is determined that another pair of a detection signature and a residual signature are not to be generated (block 810=no), then the flow proceeds to block 825. Therefore, as the flow leaves block 810 to proceed to block 825, some embodiments will have generated several pairs of detection signatures and residual signatures (e.g., a pair includes a detection signature and a residual signature), each corresponding to different detector spectral sensitivities or different illuminant spectral-power distributions.

In block 825, respective detection signatures and residual signatures for candidate materials are obtained from a database. Next, in block 830, a count j is initialized to 0. The flow then proceeds to block 835, where it is determined if the detection signatures and the residual signatures of the image are to be compared with the detection signatures and the residual signatures of another candidate material. If there are signatures for J candidate materials, then if j<J (block 835=yes), a comparison is to be performed and the flow proceeds to block 840.

In block 840, the detection signatures of the image are compared to the detection signatures of the current candidate material (the candidate material at index j). Next, in block 845 the residual signatures of the image are compared to the residual signatures of the current candidate material. Also, in some embodiments, a specific pair of a detection signature and a residual signature of the image is compared with a specific pair of a detection signature and a residual signature of a candidate material (e.g., pairs generated from similar detector spectral sensitivities or similar illuminant spectral-power distributions). The flow then moves to block 850, where the count j is incremented, and then the flow returns to block 835.

If it is determined in block 835 that another comparison is not to be performed (block 835=no), then the flow moves to block 855. In block 855, a candidate material is selected for the image based on the comparisons. Also, some embodiments of the method shown in FIG. 8 may omit the detection signatures or, alternatively, the residual signatures.

Figure 9:
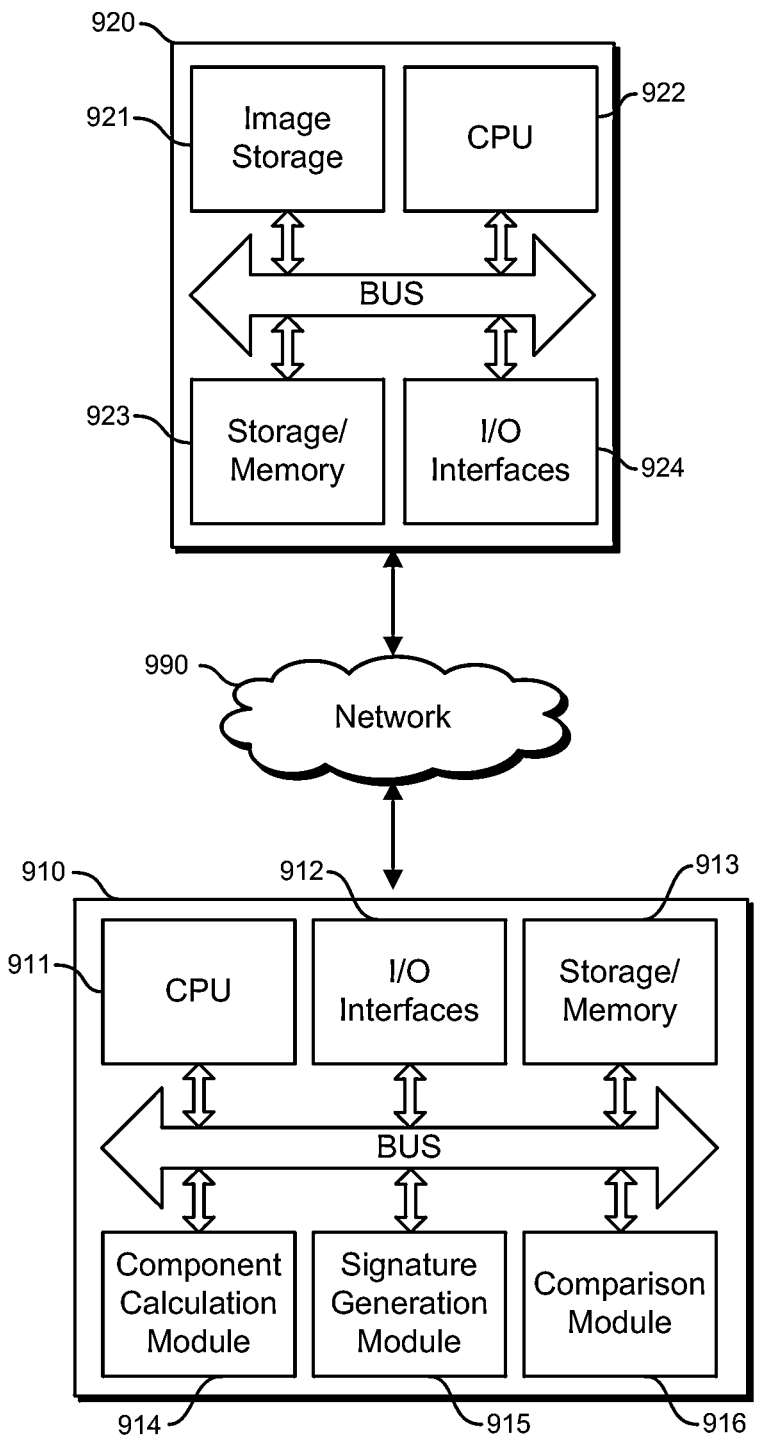
FIG. 9 illustrates an example embodiment of a system for identifying a material.

FIG. 9 illustrates an example embodiment of a system for identifying a material. The system includes a comparison device 910 and an image storage device 920. The comparison device 910 includes one or more processors (CPU) 911, I/O interfaces 912, and storage/memory 913. The CPU 911 includes one or more central processing units, which include microprocessors (e.g., a single core microprocessor, a multi-core microprocessor) and other circuits, and is configured to read and perform computer-executable instructions, such as instructions stored in storage or in memory (e.g., one or more modules that are stored in storage or memory). The computer-executable instructions may include those for the performance of the methods described herein. The I/O interfaces 912 include communication interfaces to input and output devices, which may include a keyboard, a display, a mouse, a printing device, a touch screen, a light pen, an optical storage device, a scanner, a microphone, a camera, a drive, and a network (either wired or wireless).

The storage/memory 913 includes one or more computer-readable or computer-writable media, for example a computer-readable storage medium or a transitory computer-readable medium. A computer-readable storage medium is a tangible article of manufacture, for example, a magnetic disk (e.g., a floppy disk, a hard disk), an optical disc (e.g., a CD, a DVD, a Blu-ray), a magneto-optical disk, a magnetic tape, and semiconductor memory (e.g., a non-volatile memory card, flash memory, a solid state drive, SRAM, DRAM, EPROM, EEPROM). A transitory computer-readable medium, for example a transitory propagating signal (e.g., a carrier wave), carries computer-readable information. The storage/memory 913 is configured to store computer-readable information or computer-executable instructions, including, for example, detector spectral sensitivities, illuminant spectral-power distributions, detection components, residual components, basis functions, detection signatures, residual signatures, and material signatures. The components of the comparison device 910 communicate via a bus.

The comparison device 910 also includes a component-calculation module 914, a signature-generation module 915, and a comparison module 916. In some embodiments, the comparison device 910 includes additional or fewer modules, the modules are combined into fewer modules, or the modules are divided into more modules. The component-calculation module 914 includes instructions that, when executed by the comparison device 910, cause the comparison device 910 to obtain one or more images (e.g., from the image storage device 920), and calculate one or more of a detection component and a residual component for the image. The signature-generation module 915 includes instructions that, when executed by the comparison device 910, cause the comparison device 910 to generate one or more detection signature, residual signature, or material signature for an image (i.e., an object in the image). The comparison module 916 includes instructions that, when executed by the comparison device 910, cause the comparison device 910 to compare signatures (e.g., detection signatures, residual signatures, or material signatures) and estimate a material based on the comparison.

The image storage device 920 includes a CPU 922, storage/memory 923, I/O interfaces 924, and image storage 921. The image storage 921 includes one or more computer-readable media that are configured to store images. The image storage device 920 and the comparison device 910 communicate via a network 990.

Figure 10A:
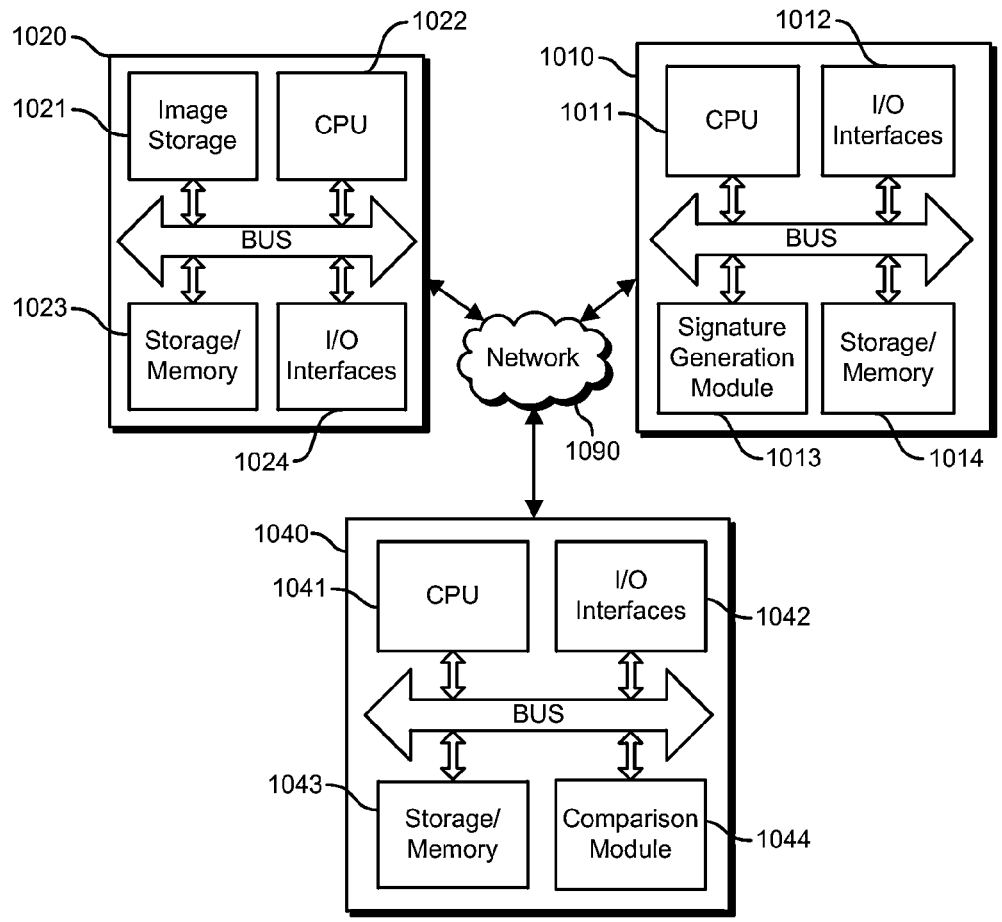
FIG. 10A illustrates an example embodiment of a system for identifying a material.

FIG. 10A illustrates an example embodiment of a system for identifying a material. The system includes an image storage device 1020, a signature-generation device 1010, and a diffusion-mapping device 1040, which communicate via a network 1090. The image storage device 1020 includes one or more CPUs 1022, I/O interfaces 1024, storage/memory 1023, and image storage 1021. The signature-generation device 1010 includes one or more CPUs 1011, I/O interfaces 1012, storage/memory 1014, and a signature-generation module 1013, which combines the functionality of the component-calculation module 914 and the signature-generation module 915 of FIG. 9. The diffusion-mapping device includes one or more CPUs 1041, I/O interfaces 1042, storage/memory 1043, and a comparison module 1044.

Figure 10B:
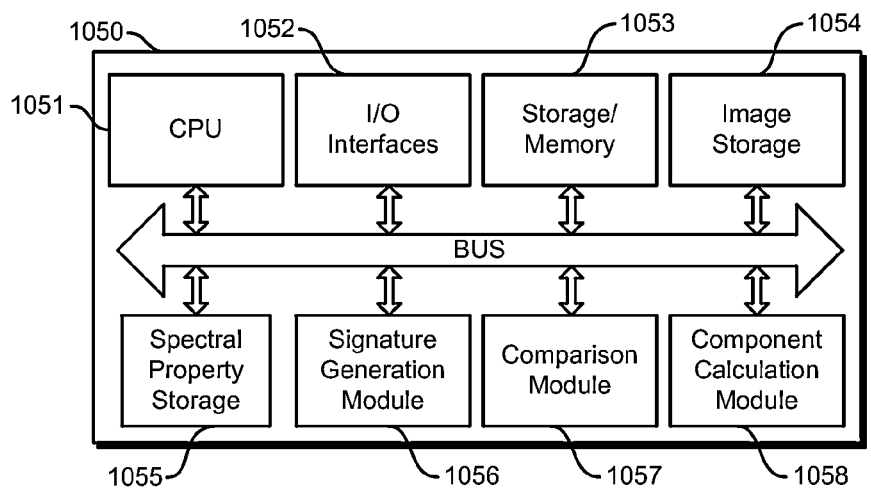
FIG. 10B illustrates an example embodiment of a system for identifying a material.

FIG. 10B illustrates an example embodiment of a system for identifying a material. The system includes a comparison device 1050. The comparison device 1050 includes one or more CPUs 1051, I/O interfaces 1052, storage/memory 1053, an image storage module 1054, a spectral-property storage module 1055, a signature-generation module 1056, a comparison module 1057, and a component-calculation module 1058. The spectral-property storage module 1055 stores detector spectral sensitivities and illuminant spectral-power distributions. Thus, this example embodiment of the comparison device 1050 performs all the operations and stores all the applicable information on a single device.

Figure 12:
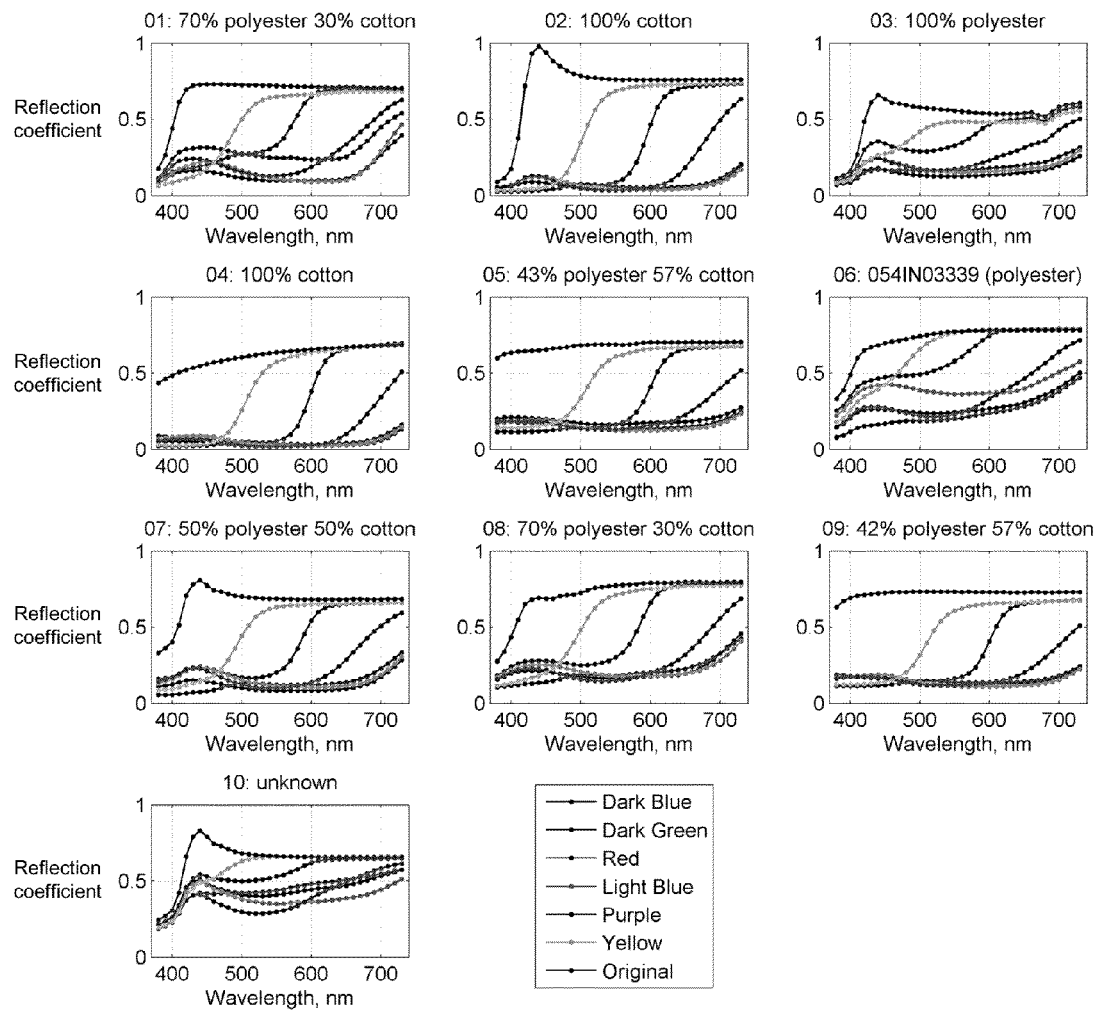
FIG. 12 illustrates an example of spectral reflectances of materials in a candidate material dataset.

FIG. 11 illustrates an example embodiment of a candidate material dataset, which may be stored in a database. The original textiles are specified in the dataset. Six different dyes (Dark Blue (Navy Blue), Dark Green (Dark Green), Red (Scarlet), Light Blue (Royal Blue), Purple (Purple), and Yellow (Lemon Yellow)) were used to dye the samples, and there are 7 samples per textile, considering the un-dyed original samples. Also, the materials are numbered 1-10, and these numberings are consistent from FIG. 11 to FIG. 15. The spectral reflectance of each sample material was measured, and the results are shown in FIG. 12, which illustrates an example of spectral reflectances of materials in a candidate material dataset. A correlation analysis was performed for an unknown material (material 10) on the materials in the dataset for all 36 channels of sampling, and the correlation results are presented in FIG. 13, which illustrates examples of spectral reflectance correlations between a material and materials in a candidate material dataset. The average correlation results were generated across all 7 samples, including the original material and the material dyed with 6 different colors. In a row in FIG. 13, the top value is the minimum correlation, the middle value is the average correlation, and the bottom value is the maximum correlation.

According to the average correlation results, the most likely material composition of the unknown material (material 10) is material 3, as indicated by a correlation of 0.919 based on average values. This is consistent with a visual comparison of the plots of material 10 and material 3. However, by just examining spectral correlation, differentiating most of the other materials may be difficult because all the materials have a relatively high average spectral correlation with the unknown material (material 10).

Thus, in addition to the overall spectral correlation analysis, a correlation analysis using decomposition was performed that included generating correlation coefficients for detection component coefficients and residual component coefficients. The residual component coefficients were metameric black component coefficients. The detection component correlation results are shown in FIG. 14, which illustrates examples of spectral reflectance correlations between a material and materials in a candidate material dataset. The detection components were calculated using three channels (e.g., for the fundamental components case of the detection components uses three channels by definition). In a row, the top value is the minimum correlation, the middle value is the average correlation, and the bottom value is the maximum correlation. FIG. 14 shows that all of the detection component correlation coefficients were high, which means that they all have same color. This result was expected since the same dye was used for each set of materials.

Additionally, the correlation coefficients for the residual components (metameric black components in this example) are shown in FIG. 15, which illustrates examples of spectral reflectance correlations between a material and materials in a candidate material dataset. Thirty-six channels were used to calculate the residual components. FIG. 15 shows that the correlation coefficients for the residual components were lower, which shows that the materials are not the same in most instances. However, the average correlations between material 6 and material 9 were relatively high (0.664) since they are very similar, as shown in the curves of FIG. 12.

The cross-correlation values in FIG. 15 show the potential discrimination of each material in relation to other materials. For example, by establishing a correlation of 0.6 as a threshold for discrimination, the discrimination success rate may be calculated according to the following: (number of samples with correlation <0.6) divided by (total number of samples). If this discrimination success rate is applied to the results for materials 1-10, as shown in FIG. 13 to FIG. 15, the overall spectral correlation produces an average discrimination success rate of 5.7%, which can be improved by 78.3% through using metameric black correlation. For correlations below 0.6, the discrimination success rates for both the overall spectral correlations and the residual component correlations are shown in FIG. 16.

Figure 18:
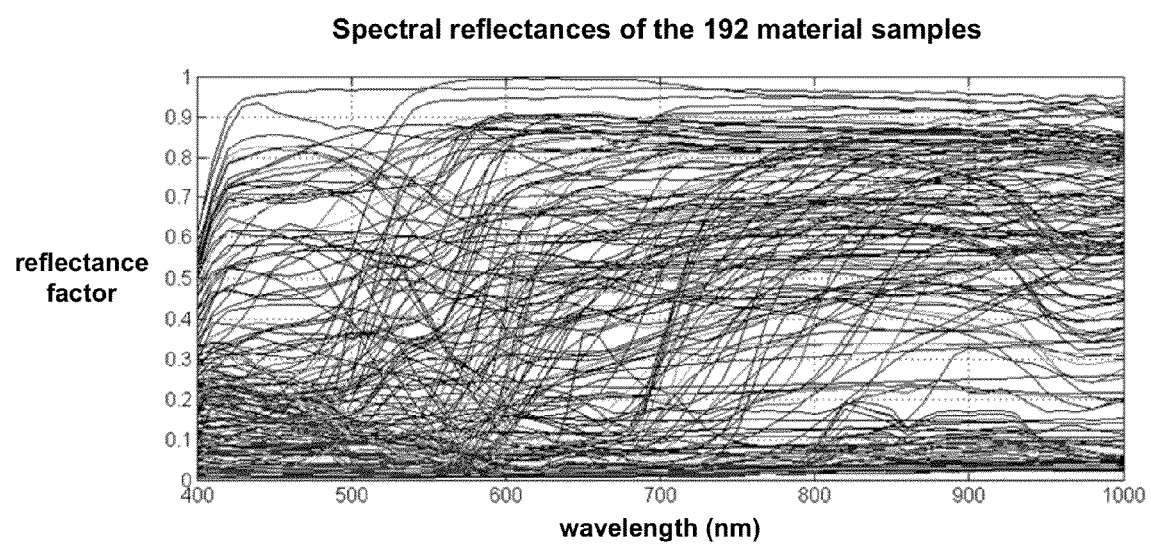
FIG. 18 illustrates an example of spectral reflectances of materials in a candidate material dataset.
Figure 19A:
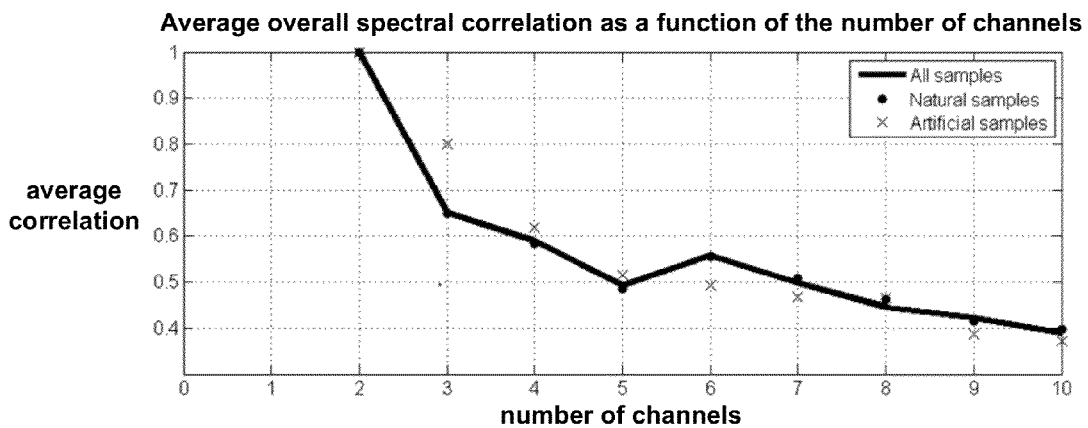
FIG. 19A shows the average overall spectral correlations for 88 natural samples and 104 man-made samples for different numbers of channels.

FIG. 17 illustrates an example embodiment of a candidate material dataset, which may be stored in a database. The dataset includes categories of natural and artificial ("man-made") objects. The spectral reflectances of 192 material samples (88 natural material samples and 104 man-made material samples) from the illustrated categories were measured, and the results are shown in FIG. 18, which illustrates an example of spectral reflectances of materials in a candidate material dataset. Also, FIG. 19A shows the average overall spectral correlations for 88 natural samples and 104 man-made samples for different numbers of channels.

Figure 19B:
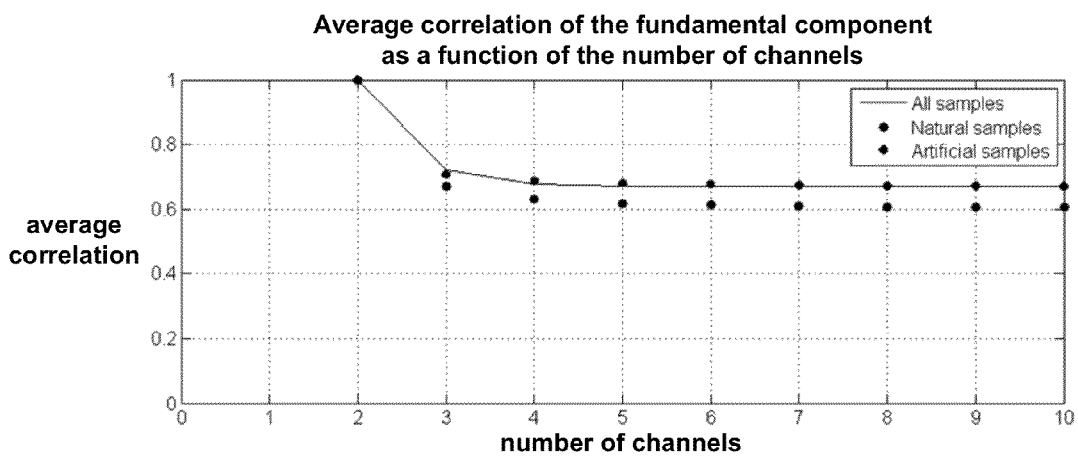
FIG. 19B shows the average correlations of material samples that were calculated based on fundamental components.

Furthermore, based on CIE 2 degree observer and D65 illuminant, the material samples were decomposed into respective fundamental components and metameric black components before calculating the correlation. FIG. 19B shows the average correlations of the material samples that were calculated based on the fundamental components. The natural material samples had slightly better discrimination performance than the whole ensemble of material samples and the man-made material samples. Also, some embodiments that use the fundamental component for the detection component do not use more than three channels because by definition the fundamental component has three channels.

Figure 19C:
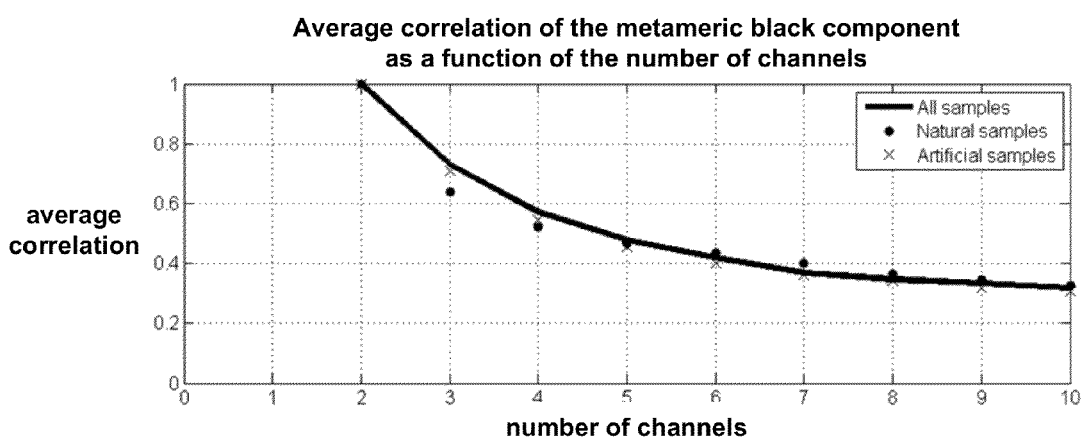
FIG. 19C shows the average correlations of material samples that were calculated based on metameric black components.

FIG. 19C shows the average correlations of the material samples that were calculated based on metameric black components. FIG. 19C shows that the metameric black component analysis has a much better discrimination performance than the fundamental component analysis.

Figure 20A:
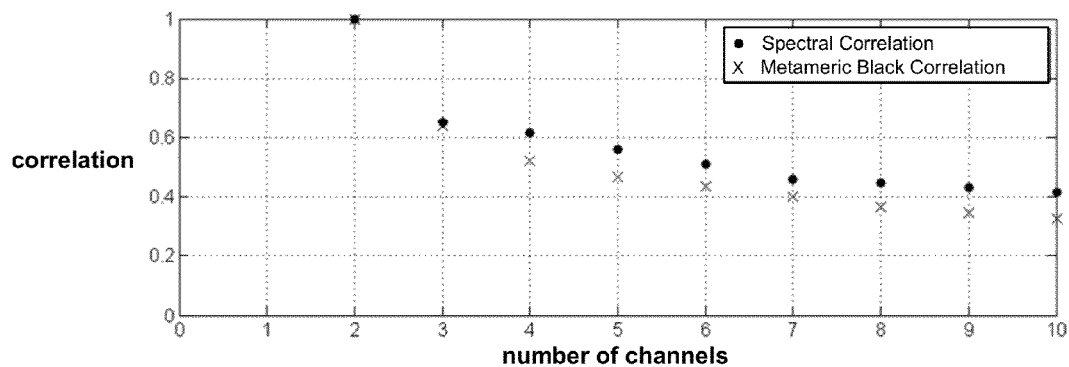
FIG. 20A shows a comparison between overall spectral correlation results and metameric black correlation results for 88 natural samples.
Figure 20B:
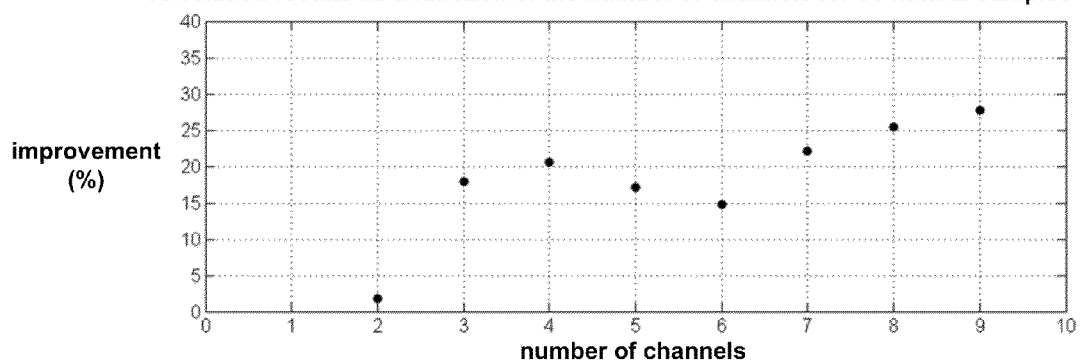
FIG. 20B shows the improvement of metameric black correlation results over overall spectral correlation results for 88 natural samples.

FIG. 20A shows a comparison between the overall spectral correlation results and the metameric black correlation results for the 88 natural samples. FIG. 20B shows the improvement of the metameric black correlation results over the overall spectral correlation results for the 88 natural samples in terms of the number of channels. The results in FIG. 20B show that for the natural material samples there is some improvement in performance using metameric black component correlation: it was possible to achieve improvements between 15% and 28% using more than 3 channels.

Figure 21A:
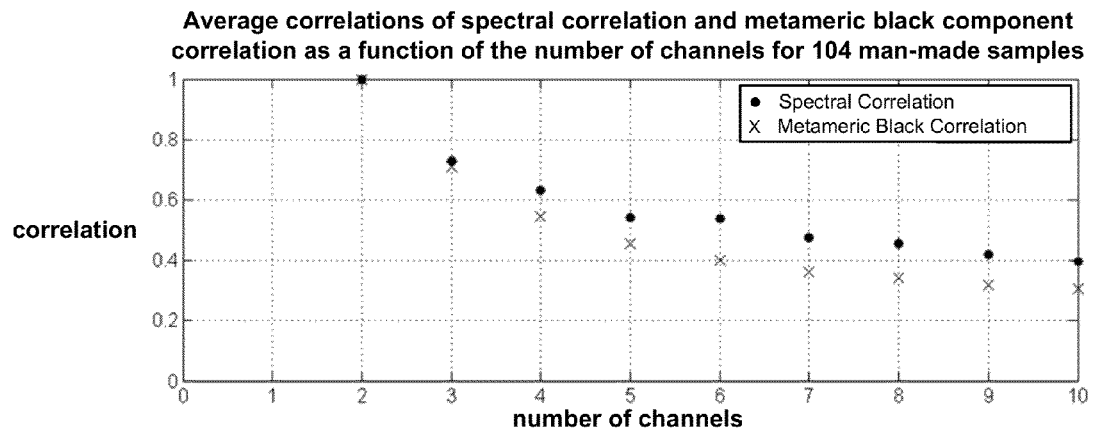
FIG. 21A shows a comparison between the results of overall spectral correlation and metameric black correlation for 104 man-made material samples.
Figure 21B:
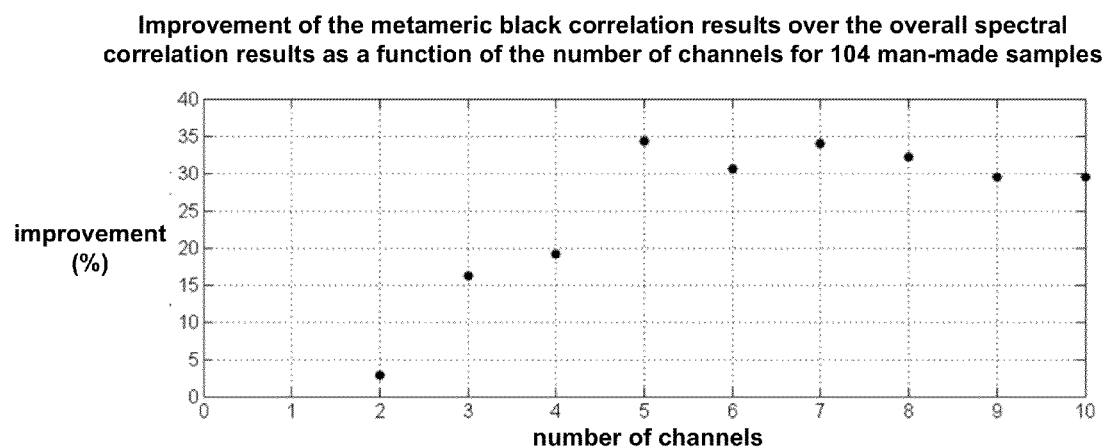
FIG. 21B shows the improvement of metameric black correlation results over overall spectral correlation results for 104 man-made material samples.

FIG. 21A shows a comparison between the results of overall spectral correlation and metameric black correlation for the 104 man-made material samples. FIG. 21B shows the improvement of the metameric black correlation results over the overall spectral correlation results for the 104 man-made material samples in terms of number of channels. The results in FIG. 21B show the great benefit of using metameric black correlation instead of spectral correlation for these man-made materials, with the results showing improvements of over 30% when using 5 or more channels. This dramatic improvement is obtained because by decomposing the spectra into fundamental and metameric black, the "color" component (related to the fundamental component) can be decoupled from a residual component. By analyzing the residual component (e.g., the metameric black component) the effects of colors that are not natural in the properties of a man-made material may be discounted.

FIG. 22 shows the discrimination success rates for examples of overall spectral correlations and residual component correlations. The discrimination success rates were generated using 6 channels for 15 representative samples that included both natural and man-made materials. The results show that using metameric black correlation may improve the discrimination rate for man-made objects, such as paints and plastics.

Figure 23A:
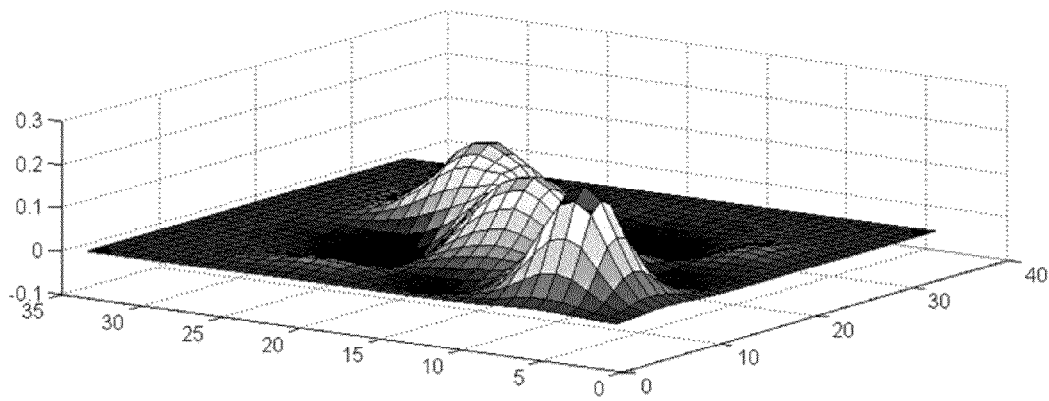
FIG. 23A illustrates a graphic representation of a transformation matrix [T].
Figure 23B:
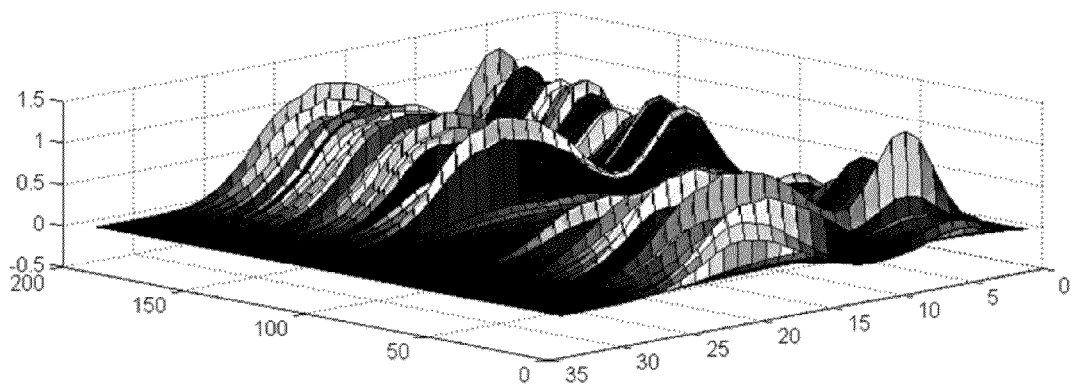
FIG. 23B shows an example of detection components.
Figure 23C:
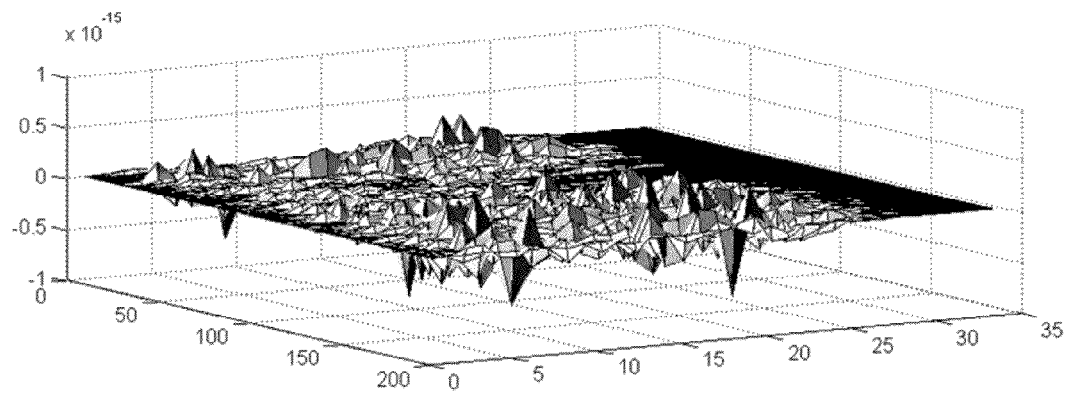
FIG. 23C shows an example of residual components.

FIG. 23A illustrates a graphic representation of a transformation matrix [T]. In the transformation matrix [T], the z-axis shows the value and the x- and y-axes show the wavelength numbers. The 3 peaks correspond to the peaks of the CIE 2 degree color matching functions combined with the spectral power distribution of CIE D65 illuminant. FIG. 23B shows an example of detection components. The example detection components (e.g., fundamental component) were calculated from the previous example. The axis on the right side represents wavelength number and the axis on the left side represents sample number. FIG. 23C shows an example of residual components. The example residual components (e.g., metameric black component) were calculated from the previous example. In FIG. 23C, the axis on the right side represents wavelength number and the axis on the left side represents sample number.

The above-described devices, systems, and methods can be implemented by supplying one or more computer-readable media that contain computer-executable instructions for realizing the above-described operations to one or more computing devices that are configured to read and execute the computer-executable instructions. Thus, the systems or devices perform the operations of the above-described embodiments when executing the computer-executable instructions. Also, an operating system on the one or more systems or devices may implement at least some of the operations of the above-described embodiments. Thus, the computer-executable instructions or the one or more computer-readable media that contain the computer-executable instructions constitute an embodiment.

Any applicable computer-readable medium (e.g., a magnetic disk (including a floppy disk, a hard disk), an optical disc (including a CD, a DVD, a Blu-ray disc), a magneto-optical disk, a magnetic tape, and semiconductor memory (including flash memory, DRAM, SRAM, a solid state drive, EPROM, EEPROM)) can be employed as a computer-readable medium for the computer-executable instructions. The computer-executable instructions may be stored on a computer-readable storage medium that is provided on a function-extension board inserted into a device or on a function-extension unit connected to the device, and a CPU provided on the function-extension board or unit may implement at least some of the operations of the above-described embodiments.

The scope of the claims is not limited to the above-described embodiments and includes various modifications and equivalent arrangements. Also, as used herein, the conjunction "or" generally refers to an inclusive "or," though "or" may refer to an exclusive "or" if expressly indicated or if the context indicates that the "or" must be an exclusive "or."

What is claimed is:

1. A method comprising:
    obtaining an image;
    estimating a spectral image of the obtained image;
    calculating one or both of a detection component of the image and a residual component of the image, wherein the detection component of the image is calculated based on the spectral image, a spectral-power distribution for a specific illuminant, and spectral sensitivities of a detector, and wherein the residual component of the image is calculated based on the spectral image, the spectral power distribution for the specific illuminant, and the spectral sensitivities of the detector or is calculated based on the spectral image and the calculated detection component; and
    generating an image signature based on one or both of
        the detection component and detection-component basis functions, and
        the residual component and residual-component basis functions.

2. The method of claim 1, further comprising identifying one or more materials in the image based on the image signature.

3. The method of claim 1, wherein generating the image signature based on the detection component and the detection-component basis functions includes calculating coefficients of the detection-component basis functions based on the detection component and on the detection-component basis functions, and
    wherein generating the image signature based on the residual component and the residual-component basis functions includes calculating coefficients of the residual-component basis functions based on the residual component and on the residual-component basis functions.

4. The method of claim 3, wherein calculating the coefficients of the detection-component basis functions includes decomposing the detection component into the detection-component basis functions; and
    wherein calculating the coefficients of the residual-component basis functions includes decomposing the residual component into the residual-component basis functions.

5. The method of claim 3, further comprising:
    generating a colorimetric signature based on the coefficients of the detection-component basis functions; and
    generating a spectral signature based on the coefficients of the residual-component basis functions, wherein
    the image signature is generated based on the colorimetric signature and the spectral signature.

6. The method of claim 1, wherein both the detection component of the image and the residual component of the image are calculated, and
    wherein the image signature is generated based on both of
        the detection component and the detection-component basis functions, and
        the residual component and the residual-component basis functions.

7. The method of claim 6, wherein generating the image signature includes calculating both of coefficients of the detection-component basis functions and coefficients of the residual-component basis functions.

8. The method of claim 1, wherein the detection component is a fundamental component and wherein the residual component is a metameric black component.

9. A system for generating a spectral signature, the system comprising:
    one or more computer-readable media; and
    one or more processors configured to cause the system to perform operations including
        obtaining an image,
        generating a spectral reflectance estimate of the image,
        calculating one or both of a detection component and a residual component, wherein the detection component is calculated based on the spectral reflectance estimate of the image, a spectral-power distribution for a specific illuminant, and detector spectral sensitivities, and wherein the residual component is calculated based on the spectral reflectance estimate of the image and the calculated detection component or is calculated based on the spectral reflectance estimate of the image, the spectral power distribution for the specific illuminant, and the detector spectral sensitivities, and
        generating one or both of a detection-component signature and a residual-component signature, wherein the detection component signature is generated based on the detection component and on detection-component basis functions, and wherein the residual-component signature is generated based on the residual component and on residual-component basis functions.

10. The system of claim 9, wherein, to generate the detection-component signature, the one or more processors are further configured to cause the system to calculate coefficients of the detection-component basis functions based on the detection component and on the detection-component basis functions, and
    wherein, to generate the residual-component signature, the one or more processors are further configured to cause the system to calculate coefficients of the residual-component basis functions based on the residual component and on the residual-component basis functions.

11. The system of claim 10, wherein, to calculate the coefficients of the detection-component basis functions, the one or more processors are further configured to cause the system to decompose the detection component into the detection-component basis functions, and wherein, to calculate the coefficients of the residual-component basis functions, the one or more processors are further configured to cause the system to decompose the residual component into the residual-component basis functions.

12. The system of claim 11, wherein the one or more processors are further configured to cause the system to perform operations comprising:

obtaining one or both of respective detection-component signatures and respective residual-component signatures for one or more candidate materials; and selecting a candidate material for the image based on the detection-component signature for the image and the detection-component signatures for the candidate images, on the residual-component signature for the image and the residual-component signatures for the candidate images, or on both.

13. One or more non-transitory computer-readable media storing instructions that, when executed by one or more computing devices, cause the one or more computing devices to perform operations comprising:

obtaining an image;

generating a spectral image of the obtained image;

calculating one or more of a detection component and a residual component, wherein the detection component is calculated based on the spectral image, a spectral-power distribution for a specific illuminant, and detector spectral sensitivities, and wherein the residual component is calculated based on the spectral image and the calculated detection component or is calculated based on the spectral image, the spectral power distribution for the specific illuminant, and the detector spectral sensitivities; and generating an image signature based on at least one of
the detection component and detection-component basis functions, and
the residual component and residual-component basis functions.

14. The one or more non-transitory computer-readable media of claim 13, wherein the operations include calculating both the detection component and the residual component.

15. The one or more non-transitory computer-readable media of claim 13, wherein generating the image signature based on the detection component and the detection-component basis functions includes calculating coefficients of the detection-component basis functions based on the detection component and on the detection-component basis functions, and wherein generating the image signature based on the residual component and the residual-component basis functions includes calculating coefficients of the residual-component basis functions based on the residual component and on the residual-component basis functions.

16. The one or more non-transitory computer-readable media of claim 15, wherein generating the image signature includes one or both of generating a colorimetric signature based on the coefficients of the detection-component basis functions and generating a spectral signature based on the coefficients of the residual-component basis functions.

17. The one or more non-transitory computer-readable media of claim 16, wherein the operations further comprise comparing the spectral signature to a collection of corresponding spectral signatures of candidate materials, and identifying a material in the image based on the comparisons.

18. The one or more non-transitory computer-readable media of claim 17, wherein comparing the spectral signature to a collection of corresponding spectral signatures of candidate materials is based on a spectral matching probability function.

19. The one or more non-transitory computer-readable media of claim 15, wherein calculating the coefficients of the residual-component basis functions includes decomposing the residual component into the residual-component basis functions.

20. The one or more non-transitory computer-readable media of claim 19, wherein calculating the coefficients of the detection-component basis functions includes decomposing the detection component into the detection-component basis functions.

* * * * *